(12) United States Patent
Riebe et al.

(10) Patent No.: US 12,151,061 B2
(45) Date of Patent: Nov. 26, 2024

(54) AEROSOL DELIVERY SYSTEMS AND RELATED METHODS

(71) Applicant: Pearl Therapeutics, Inc., Redwood City, CA (US)

(72) Inventors: Michael Riebe, Durham, NC (US); Daniel Deaton, Durham, NC (US); Matthew Ferriter, Durham, NC (US); Jill Karen Sherwood, Durham, NC (US); John Hainsworth, Cambridge (GB); Fred William Hamlin, Cambridge (GB); Ralph Lamble, Cottenham (GB); Scott Lewis, Cambridge (GB); George McGee Perkins, Cambridge (GB)

(73) Assignee: PEARL THERAPEUTICS, INC., Redwood City, CA (US)

( * ) Notice: Subject to any disclaimer, the term of this patent is extended or adjusted under 35 U.S.C. 154(b) by 839 days.

(21) Appl. No.: 17/323,824

(22) Filed: May 18, 2021

(65) Prior Publication Data

US 2021/0369987 A1    Dec. 2, 2021

Related U.S. Application Data

(63) Continuation of application No. 15/743,239, filed as application No. PCT/US2016/043004 on Jul. 19, 2016, now Pat. No. 11,040,156.

(Continued)

(51) Int. Cl.
*A61M 15/00*    (2006.01)

(52) U.S. Cl.
CPC ........ *A61M 15/009* (2013.01); *A61M 15/008* (2014.02); *A61M 15/0081* (2014.02);

(Continued)

(58) Field of Classification Search
CPC ................. A24F 40/42; A61M 15/009; A61M 2205/8206; A61M 15/00; A61M 15/0071
See application file for complete search history.

(56) References Cited

U.S. PATENT DOCUMENTS 5,224,472 A    7/1993  Pesenti et al.
5,284,133 A    2/1994  Burns et al.
(Continued)

FOREIGN PATENT DOCUMENTS

CN    1303309 A    7/2001
EP    1 051 984 A2    11/2000
(Continued)

OTHER PUBLICATIONS

US 7,284,551 B2, 10/2007, Jones et al. (withdrawn)
(Continued)

*Primary Examiner* — Margaret M Luarca
(74) *Attorney, Agent, or Firm* — Seed IP Law Group LLP

(57) ABSTRACT

There is provided an electronically controlled, motor-driven, breath actuated metered dose inhaler for delivering aerosolized medicament or other matter to a user. The inhaler may comprise a base housing including a motor-driven actuator and other system components and a removable aerosol cartridge insertably receivable in the base housing. The inhaler may be paired with a smart phone or other client computing device to provide additional functionality, such as to provide instructional information and feedback regarding usage of the inhaler, to generate and display dosage tracking information, and to provide alerts and reminders to a user of the inhaler or others.

28 Claims, 12 Drawing Sheets

Related U.S. Application Data

(60) Provisional application No. 62/212,379, filed on Aug. 31, 2015, provisional application No. 62/194,701, filed on Jul. 20, 2015.

(52) U.S. Cl.
CPC ... *A61M 2205/502* (2013.01); *A61M 2205/52* (2013.01); *A61M 2205/8206* (2013.01)

(56) References Cited

U.S. PATENT DOCUMENTS

| | | |
|---|---|---|
| 5,347,998 A | 9/1994 | Hodson et al. |
| 5,363,842 A | 11/1994 | Mishelevich et al. |
| 5,392,768 A | 2/1995 | Johansson et al. |
| 5,394,866 A | 3/1995 | Ritson et al. |
| 5,404,871 A | 4/1995 | Goodman et al. |
| 5,419,315 A | 5/1995 | Rubsamen |
| 5,450,336 A | 9/1995 | Rubsamen et al. |
| 5,469,750 A | 11/1995 | Lloyd et al. |
| 5,487,378 A | 1/1996 | Robertson et al. |
| 5,497,764 A | 3/1996 | Ritson et al. |
| 5,505,195 A | 4/1996 | Wolf et al. |
| 5,520,166 A | 5/1996 | Ritson et al. |
| 5,522,378 A | 6/1996 | Ritson et al. |
| 5,542,410 A | 8/1996 | Goodman et al. |
| 5,608,647 A | 3/1997 | Rubsamen et al. |
| 5,622,162 A | 4/1997 | Johansson et al. |
| 5,655,516 A | 8/1997 | Goodman et al. |
| 5,655,523 A | 8/1997 | Hodson et al. |
| 5,676,129 A | 10/1997 | Rocci, Jr. et al. |
| 5,692,492 A | 12/1997 | Bruna et al. |
| 5,694,919 A | 12/1997 | Rubsamen et al. |
| 5,694,920 A | 12/1997 | Abrams et al. |
| 5,724,986 A | 3/1998 | Jones, Jr. et al. |
| 5,743,252 A | 4/1998 | Rubsamen et al. |
| 5,755,218 A * | 5/1998 | Johansson ......... A61M 16/0858 128/200.14 |
| 5,809,997 A | 9/1998 | Wolf |
| 5,813,397 A | 9/1998 | Goodman et al. |
| 5,826,570 A | 10/1998 | Goodman et al. |
| 5,855,564 A | 1/1999 | Ruskewicz |
| 5,894,841 A | 4/1999 | Voges |
| 5,921,237 A | 7/1999 | Eisele et al. |
| 5,954,047 A * | 9/1999 | Armer ............... A61M 15/0086 128/200.14 |
| 5,971,951 A | 10/1999 | Ruskewicz |
| 6,006,747 A | 12/1999 | Eisele et al. |
| 6,012,454 A | 1/2000 | Hodson et al. |
| 6,026,808 A | 2/2000 | Armer et al. |
| 6,026,809 A | 2/2000 | Abrams et al. |
| 6,055,980 A | 5/2000 | Mecikalski et al. |
| 6,095,141 A | 8/2000 | Armer et al. |
| 6,116,238 A | 9/2000 | Jackson et al. |
| 6,119,684 A | 9/2000 | Nöhl et al. |
| 6,123,068 A | 9/2000 | Lloyd et al. |
| 6,138,669 A | 10/2000 | Rocci, Jr. et al. |
| 6,142,146 A | 11/2000 | Abrams et al. |
| 6,148,815 A | 11/2000 | Wolf |
| 6,152,130 A | 11/2000 | Abrams et al. |
| 6,196,218 B1 | 3/2001 | Voges |
| 6,234,167 B1 | 5/2001 | Cox et al. |
| 6,260,549 B1 | 7/2001 | Sosiak |
| 6,273,085 B1 | 8/2001 | Eisele et al. |
| 6,318,361 B1 | 11/2001 | Sosiak |
| 6,325,062 B1 | 12/2001 | Sosiak |
| 6,328,034 B1 | 12/2001 | Eisele et al. |
| 6,341,603 B1 | 1/2002 | Howlett |
| 6,354,290 B1 | 3/2002 | Howlett |
| 6,358,058 B1 | 3/2002 | Strupat et al. |
| 6,360,739 B1 | 3/2002 | Rand et al. |
| 6,425,392 B1 | 7/2002 | Sosiak |
| 6,431,168 B1 | 8/2002 | Rand et al. |
| 6,443,146 B1 | 9/2002 | Voges |
| 6,474,331 B1 | 11/2002 | Rand et al. |
| 6,516,796 B1 | 2/2003 | Cox et al. |
| 6,557,552 B1 | 5/2003 | Cox et al. |
| 6,601,582 B2 | 8/2003 | Rand et al. |
| 6,651,651 B1 | 11/2003 | Bonney et al. |
| D483,860 S | 12/2003 | Knoch |
| 6,656,114 B1 | 12/2003 | Poulsen et al. |
| 6,684,879 B1 | 2/2004 | Coffee et al. |
| 6,698,421 B2 | 3/2004 | Attolini |
| 6,745,761 B2 | 6/2004 | Christrup et al. |
| 6,805,116 B2 | 10/2004 | Hodson et al. |
| 6,823,863 B2 | 11/2004 | Huxham et al. |
| 6,830,046 B2 | 12/2004 | Blakley et al. |
| 6,854,461 B2 | 2/2005 | Nichols et al. |
| 6,871,535 B2 | 3/2005 | Blakley et al. |
| 6,889,690 B2 | 5/2005 | Crowder et al. |
| 6,904,907 B2 | 6/2005 | Speldrich et al. |
| 6,933,850 B2 | 8/2005 | Garcia et al. |
| 6,958,691 B1 | 10/2005 | Anderson et al. |
| 6,978,780 B1 | 12/2005 | Marnfeldt et al. |
| 6,981,499 B2 | 1/2006 | Anderson et al. |
| 6,983,652 B2 | 1/2006 | Blakley et al. |
| 6,985,798 B2 | 1/2006 | Crowder et al. |
| 7,021,560 B2 | 4/2006 | Gray et al. |
| 7,047,964 B2 | 5/2006 | Bacon |
| 7,066,029 B2 | 6/2006 | Beavis et al. |
| 7,107,986 B2 | 9/2006 | Rand et al. |
| 7,117,867 B2 | 10/2006 | Cox et al. |
| 7,118,010 B2 | 10/2006 | Crowder et al. |
| 7,146,977 B2 | 12/2006 | Beavis et al. |
| 7,191,777 B2 | 3/2007 | Brand et al. |
| 7,219,664 B2 | 5/2007 | Ruckdeschel et al. |
| 7,225,805 B2 | 6/2007 | Bacon |
| 7,252,085 B2 | 8/2007 | Kunschir |
| 7,282,029 B1 | 10/2007 | Poulsen et al. |
| 7,305,984 B2 | 12/2007 | Altobelli et al. |
| 7,322,355 B2 | 1/2008 | Jones et al. |
| 7,347,200 B2 | 3/2008 | Jones et al. |
| 7,347,202 B2 | 3/2008 | Aslin et al. |
| 7,367,333 B2 | 5/2008 | Hodson et al. |
| 7,380,550 B2 | 6/2008 | Sexton et al. |
| 7,383,740 B2 | 6/2008 | Krasilchikov et al. |
| 7,383,837 B2 | 6/2008 | Robertson et al. |
| 7,387,121 B2 | 6/2008 | Harvey |
| 7,418,961 B2 | 9/2008 | Jones et al. |
| 7,428,446 B2 | 9/2008 | Crowder et al. |
| 7,458,373 B2 | 12/2008 | Nichols et al. |
| 7,461,650 B1 | 12/2008 | Rand |
| 7,467,629 B2 | 12/2008 | Rand |
| 7,472,701 B2 | 1/2009 | Pfichner et al. |
| 7,481,213 B2 | 1/2009 | Childers |
| 7,520,278 B2 | 4/2009 | Crowder et al. |
| 7,562,657 B2 | 7/2009 | Blanch et al. |
| 7,597,099 B2 | 10/2009 | Jones et al. |
| 7,607,435 B2 | 10/2009 | Lipp |
| 7,677,411 B2 | 3/2010 | Crowder et al. |
| 7,743,765 B2 | 6/2010 | Hodson et al. |
| 7,784,459 B2 | 8/2010 | Abrams |
| 7,806,116 B2 | 10/2010 | Altobelli et al. |
| 7,814,902 B2 | 10/2010 | Abrams |
| 7,819,116 B2 | 10/2010 | Brand et al. |
| 7,832,394 B2 | 11/2010 | Schechter et al. |
| 7,837,648 B2 | 11/2010 | Blair et al. |
| 7,886,934 B2 | 2/2011 | Lu et al. |
| 7,896,002 B2 | 3/2011 | Watanabe |
| 8,044,778 B2 | 10/2011 | Monroe |
| 8,056,556 B2 | 11/2011 | Childers et al. |
| 8,082,917 B2 | 12/2011 | Ooida |
| 8,082,918 B2 | 12/2011 | Jansen et al. |
| 8,082,919 B2 | 12/2011 | Brunnberg et al. |
| 8,091,545 B2 | 1/2012 | Schechter et al. |
| 8,109,266 B2 | 2/2012 | Addington et al. |
| 8,146,592 B2 | 4/2012 | Voege et al. |
| 8,210,172 B2 | 7/2012 | Crowder et al. |
| 8,212,658 B2 | 7/2012 | Monroe |
| 8,240,301 B2 | 8/2012 | Spaargaren et al. |
| 8,240,303 B2 | 8/2012 | Hamano |
| 8,245,704 B2 | 8/2012 | Rand et al. |
| 8,291,902 B2 | 10/2012 | Abrams |
| 8,314,591 B2 | 11/2012 | Terry et al. |

(56) References Cited

U.S. PATENT DOCUMENTS

| | | |
|---|---|---|
| 8,333,190 B2 | 12/2012 | Addington et al. |
| 8,342,172 B2 | 1/2013 | Levy et al. |
| 8,357,114 B2 | 1/2013 | Poutiatine et al. |
| 8,408,208 B2 | 4/2013 | Bacon |
| 8,424,517 B2 | 4/2013 | Sutherland et al. |
| 8,464,707 B2 | 6/2013 | Jongejan et al. |
| 8,474,452 B2 | 7/2013 | Gumaste et al. |
| 8,511,299 B2 | 8/2013 | Altobelli et al. |
| 8,539,945 B2 | 9/2013 | Solomon et al. |
| 8,544,466 B2 | 10/2013 | Blanch et al. |
| 8,544,645 B2 | 10/2013 | Edwards et al. |
| 8,567,394 B2 | 10/2013 | Herder et al. |
| 8,573,203 B2 | 11/2013 | Addington et al. |
| 8,584,668 B2 | 11/2013 | Hodson et al. |
| 8,640,971 B2 | 2/2014 | Feriani et al. |
| 8,671,934 B2 | 3/2014 | Addington et al. |
| 8,712,794 B2 | 4/2014 | Hyde et al. |
| 8,739,790 B2 | 6/2014 | Bruna |
| 8,746,238 B2 | 6/2014 | Kohnle |
| 8,763,606 B2 | 7/2014 | Mosier et al. |
| 8,800,559 B2 | 8/2014 | Bowman et al. |
| 8,800,819 B2 | 8/2014 | Carriço et al. |
| 8,807,131 B1 | 8/2014 | Tunnell et al. |
| 8,910,625 B2 | 12/2014 | Mullinger et al. |
| 8,978,966 B2 | 3/2015 | Walsh et al. |
| 8,985,101 B2 | 3/2015 | Mosier |
| 8,991,390 B2 | 3/2015 | Akouka et al. |
| 9,004,062 B2 | 4/2015 | Lang et al. |
| 9,035,765 B2 | 5/2015 | Engelhard et al. |
| 9,060,715 B2 | 6/2015 | Schipper et al. |
| 9,072,464 B2 | 7/2015 | Haartsen et al. |
| 9,072,846 B2 | 7/2015 | Helmlinger |
| 9,095,175 B2 | 8/2015 | Terry et al. |
| 9,108,010 B2 | 8/2015 | Walsh et al. |
| 9,152,829 B2 | 10/2015 | Day et al. |
| 9,162,031 B2 | 10/2015 | Gumaste et al. |
| 9,174,013 B2 | 11/2015 | Walsh et al. |
| 9,216,260 B2 | 12/2015 | Walsh et al. |
| 9,227,029 B2 | 1/2016 | Addington et al. |
| 9,242,056 B2 | 1/2016 | Andersen et al. |
| 11,040,156 B2 | 6/2021 | Riebe et al. |
| 2001/0032644 A1 | 10/2001 | Hodson et al. |
| 2002/0011247 A1 | 1/2002 | Ivri et al. |
| 2002/0026938 A1 | 3/2002 | Hodson et al. |
| 2002/0040713 A1 | 4/2002 | Eisele et al. |
| 2002/0090601 A1 | 7/2002 | Strupat et al. |
| 2002/0123669 A1 | 9/2002 | Wickstrom |
| 2002/0189612 A1 | 12/2002 | Rand |
| 2002/0189615 A1 | 12/2002 | Henry et al. |
| 2003/0065536 A1 | 4/2003 | Hansen et al. |
| 2003/0079744 A1 | 5/2003 | Bonney et al. |
| 2003/0168057 A1 | 9/2003 | Snyder et al. |
| 2004/0025871 A1 | 2/2004 | Davies |
| 2004/0050385 A1 | 3/2004 | Bonney et al. |
| 2004/0065326 A1 | 4/2004 | MacMichael et al. |
| 2004/0079360 A1 | 4/2004 | Coffee et al. |
| 2004/0089299 A1 | 5/2004 | Bonney et al. |
| 2004/0094152 A1 | 5/2004 | Harvey et al. |
| 2004/0231667 A1 | 11/2004 | Horton et al. |
| 2004/0255936 A1 | 12/2004 | Urbanus |
| 2005/0022806 A1 | 2/2005 | Beaumont et al. |
| 2005/0028815 A1 | 2/2005 | Deaton et al. |
| 2005/0119604 A1 | 6/2005 | Bonney et al. |
| 2005/0133024 A1 | 6/2005 | Coifman |
| 2005/0161467 A1 | 7/2005 | Jones |
| 2005/0172958 A1 | 8/2005 | Singer et al. |
| 2005/0197621 A1 | 9/2005 | Poulsen et al. |
| 2005/0251289 A1 | 11/2005 | Bonney et al. |
| 2005/0274378 A1 | 12/2005 | Bonney et al. |
| 2006/0130829 A1 | 6/2006 | Sexton et al. |
| 2006/0213505 A1 | 9/2006 | Hodson et al. |
| 2006/0237009 A1 | 10/2006 | Jones et al. |
| 2006/0254581 A1 | 11/2006 | Genova et al. |
| 2006/0278225 A1 | 12/2006 | MacMichael et al. |
| 2006/0289005 A1 | 12/2006 | Jones et al. |
| 2007/0017506 A1 | 1/2007 | Bell et al. |
| 2007/0056585 A1 | 3/2007 | Davies et al. |
| 2007/0074722 A1 | 4/2007 | Giroux et al. |
| 2007/0125372 A1 | 6/2007 | Chen |
| 2007/0135691 A1 | 6/2007 | Zingelewicz et al. |
| 2007/0186923 A1 | 8/2007 | Poutiatine et al. |
| 2007/0227534 A1 | 10/2007 | Nobutani et al. |
| 2007/0295329 A1 | 12/2007 | Lieberman et al. |
| 2008/0017189 A1 | 1/2008 | Ruckdeschel et al. |
| 2008/0030309 A1 | 2/2008 | Darrouzet |
| 2008/0173301 A1 | 7/2008 | Deaton et al. |
| 2008/0177154 A1 | 7/2008 | Hansen et al. |
| 2008/0177155 A1 | 7/2008 | Hansen et al. |
| 2008/0178872 A1 | 7/2008 | Genova et al. |
| 2008/0223362 A1* | 9/2008 | Hamano .................. A61L 9/14 128/200.23 |
| 2008/0228099 A1 | 9/2008 | Abrams et al. |
| 2009/0005735 A1 | 1/2009 | Wikner et al. |
| 2009/0114219 A1 | 5/2009 | Ferris et al. |
| 2009/0151716 A1 | 6/2009 | Abrams |
| 2009/0188490 A1 | 7/2009 | Han |
| 2009/0194104 A1 | 8/2009 | Van Sickle |
| 2009/0229607 A1 | 9/2009 | Brunnberg et al. |
| 2009/0308387 A1 | 12/2009 | Andersen et al. |
| 2010/0083964 A1 | 4/2010 | Brown et al. |
| 2010/0089394 A1 | 4/2010 | Sakurada et al. |
| 2010/0094099 A1* | 4/2010 | Levy ..................... G16H 50/20 600/300 |
| 2010/0180890 A1 | 7/2010 | Nobutani |
| 2010/0192948 A1 | 8/2010 | Sutherland et al. |
| 2010/0219263 A1 | 9/2010 | Feriani et al. |
| 2010/0250280 A1 | 9/2010 | Sutherland |
| 2010/0250697 A1 | 9/2010 | Hansen et al. |
| 2010/0263665 A1 | 10/2010 | Brown et al. |
| 2010/0326436 A1 | 12/2010 | Kaneko |
| 2011/0162642 A1 | 7/2011 | Akouka et al. |
| 2011/0225008 A1 | 9/2011 | Elkouh et al. |
| 2011/0253139 A1 | 10/2011 | Guthrie et al. |
| 2012/0003928 A1 | 1/2012 | Geboers et al. |
| 2012/0012106 A1 | 1/2012 | Bari |
| 2012/0048269 A1 | 3/2012 | Pardonge et al. |
| 2012/0048270 A1 | 3/2012 | Pardonge |
| 2012/0055472 A1 | 3/2012 | Brunnberg et al. |
| 2012/0080029 A1 | 4/2012 | Koerner et al. |
| 2012/0090605 A1 | 4/2012 | McDaid et al. |
| 2012/0190999 A1 | 7/2012 | Addington et al. |
| 2012/0227737 A1 | 9/2012 | Mastrototaro et al. |
| 2012/0240923 A1 | 9/2012 | Denyer et al. |
| 2012/0255548 A1 | 10/2012 | Denny et al. |
| 2012/0285447 A1 | 11/2012 | Schipper et al. |
| 2012/0293321 A1 | 11/2012 | Monroe |
| 2013/0008436 A1 | 1/2013 | Von Hollen et al. |
| 2013/0046477 A1 | 2/2013 | Hyde et al. |
| 2013/0053719 A1 | 2/2013 | Wekell |
| 2013/0087142 A1 | 4/2013 | Kane et al. |
| 2013/0092158 A1 | 4/2013 | Levy et al. |
| 2013/0133643 A1 | 5/2013 | Hodson et al. |
| 2013/0172690 A1 | 7/2013 | Arne et al. |
| 2013/0192594 A1 | 8/2013 | Addington et al. |
| 2013/0239957 A1 | 9/2013 | Pinfold |
| 2013/0269685 A1 | 10/2013 | Wachtel et al. |
| 2013/0269688 A1 | 10/2013 | Attolini |
| 2013/0269694 A1 | 10/2013 | Patton et al. |
| 2014/0000598 A1 | 1/2014 | Sutherland et al. |
| 2014/0000602 A1 | 1/2014 | Herder et al. |
| 2014/0007016 A1 | 1/2014 | Li |
| 2014/0007867 A1 | 1/2014 | Bruin et al. |
| 2014/0032243 A1 | 1/2014 | Solomon et al. |
| 2014/0053833 A1 | 2/2014 | Cline et al. |
| 2014/0060531 A1 | 3/2014 | Brambilla et al. |
| 2014/0096711 A1 | 4/2014 | Walsh et al. |
| 2014/0096769 A1 | 4/2014 | Walsh et al. |
| 2014/0148722 A1 | 5/2014 | Addington et al. |
| 2014/0158126 A1 | 6/2014 | Parry-Billings et al. |
| 2014/0174435 A1 | 6/2014 | Addington et al. |
| 2014/0182584 A1 | 7/2014 | Sutherland et al. |
| 2014/0202457 A1 | 7/2014 | Addington et al. |
| 2014/0202458 A1 | 7/2014 | Addington et al. |
| 2014/0216444 A1 | 8/2014 | Shtram et al. |

(56) References Cited

U.S. PATENT DOCUMENTS

| | | |
|---|---|---|
| 2014/0243749 A1 | 8/2014 | Edwards et al. |
| 2014/0246034 A1 | 9/2014 | Terry et al. |
| 2014/0246035 A1 | 9/2014 | Minskoff et al. |
| 2014/0251330 A1 | 9/2014 | Collins et al. |
| 2014/0261400 A1 | 9/2014 | Addington et al. |
| 2014/0305429 A1 | 10/2014 | Lewis |
| 2014/0352690 A1 | 12/2014 | Kolb et al. |
| 2014/0373838 A1 | 12/2014 | Herder et al. |
| 2015/0059739 A1 | 3/2015 | Aslam |
| 2015/0096555 A1 | 4/2015 | Wang et al. |
| 2015/0100276 A1 | 4/2015 | Huang et al. |
| 2015/0100335 A1 | 4/2015 | Englehard et al. |
| 2015/0101604 A1 | 4/2015 | Crosbie |
| 2015/0112707 A1 | 4/2015 | Manice et al. |
| 2015/0120320 A1 | 4/2015 | Fateh |
| 2015/0134358 A1 | 5/2015 | Fisher |
| 2015/0150484 A1 | 6/2015 | Wekell |
| 2015/0165137 A1 | 6/2015 | Mullinger et al. |
| 2015/0174348 A1 | 6/2015 | Tunnell et al. |
| 2015/0174349 A1 | 6/2015 | Tunnell et al. |
| 2015/0231342 A1 | 8/2015 | Walsh et al. |
| 2015/0235548 A1 | 8/2015 | Engelhard et al. |
| 2015/0238714 A1 | 8/2015 | Walsh et al. |
| 2015/0238715 A1 | 8/2015 | Walsh et al. |
| 2015/0246190 A1 | 9/2015 | Walsh et al. |
| 2015/0246191 A1 | 9/2015 | Walsh et al. |
| 2015/0246192 A1 | 9/2015 | Walsh et al. |
| 2015/0246193 A1 | 9/2015 | Walsh et al. |
| 2015/0249478 A1 | 9/2015 | Greiner |
| 2015/0273164 A1 | 10/2015 | Schipper et al. |
| 2015/0273165 A1 | 10/2015 | Hadash |
| 2015/0294551 A1 | 10/2015 | Edwards et al. |
| 2015/0297843 A1 | 10/2015 | Lu et al. |
| 2015/0335834 A1 | 11/2015 | Anandhakrishnan |
| 2015/0352281 A1 | 12/2015 | Pfrang |
| 2016/0001018 A1 | 1/2016 | Fink et al. |
| 2016/0001021 A1 | 1/2016 | Gumaste et al. |
| 2016/0019498 A1 | 1/2016 | Bhalodia et al. |
| 2017/0325734 A1 | 11/2017 | Sutherland et al. |

FOREIGN PATENT DOCUMENTS

| | | |
|---|---|---|
| EP | 1 358 902 A1 | 11/2003 |
| EP | 1 144 028 B1 | 6/2004 |
| EP | 1 726 322 A1 | 11/2006 |
| EP | 1 224 600 B1 | 6/2007 |
| EP | 2 514 463 A2 | 10/2012 |
| EP | 2 456 493 B1 | 6/2013 |
| EP | 2 638 925 A1 | 9/2013 |
| EP | 2 514 464 B1 | 7/2015 |
| KR | 10-2008-0030563 A | 4/2008 |
| WO | 92/07600 A1 | 5/1992 |
| WO | 92/15353 A2 | 9/1992 |
| WO | 93/12823 A2 | 7/1993 |
| WO | 94/16756 A1 | 8/1994 |
| WO | 95/07724 A1 | 3/1995 |
| WO | 98/41265 A1 | 9/1998 |
| WO | 99/08737 A1 | 2/1999 |
| WO | 99/49920 A1 | 10/1999 |
| WO | 00/35524 A2 | 6/2000 |
| WO | 01/26021 A1 | 4/2001 |
| WO | 02/100468 A2 | 12/2002 |
| WO | 03/043684 A1 | 5/2003 |
| WO | 03/059413 A2 | 7/2003 |
| WO | 03/063754 A1 | 8/2003 |
| WO | 03/095010 A2 | 11/2003 |
| WO | 2004/011068 A1 | 2/2004 |
| WO | 2005/025654 A1 | 3/2005 |
| WO | 2006/012205 A2 | 2/2006 |
| WO | 2006/048417 A1 | 5/2006 |
| WO | 2006/124517 A1 | 11/2006 |
| WO | 2007/137991 A1 | 12/2007 |
| WO | 2008/079350 A2 | 7/2008 |
| WO | 2009/022139 A1 | 2/2009 |
| WO | 2010/002421 A1 | 1/2010 |
| WO | 2010/107912 A1 | 9/2010 |
| WO | 2012/022771 A2 | 2/2012 |
| WO | 2012/100164 A1 | 7/2012 |
| WO | 2013/098334 A1 | 7/2013 |
| WO | 2014/159016 A1 | 10/2014 |

OTHER PUBLICATIONS

Murphy et al., "Therapeutic equivalence of budesonide/formoterol delivered via breath-actuated inhaler vs pMDI," *Respiratory Medicine* 109(2):1-10, 2015.

\* cited by examiner

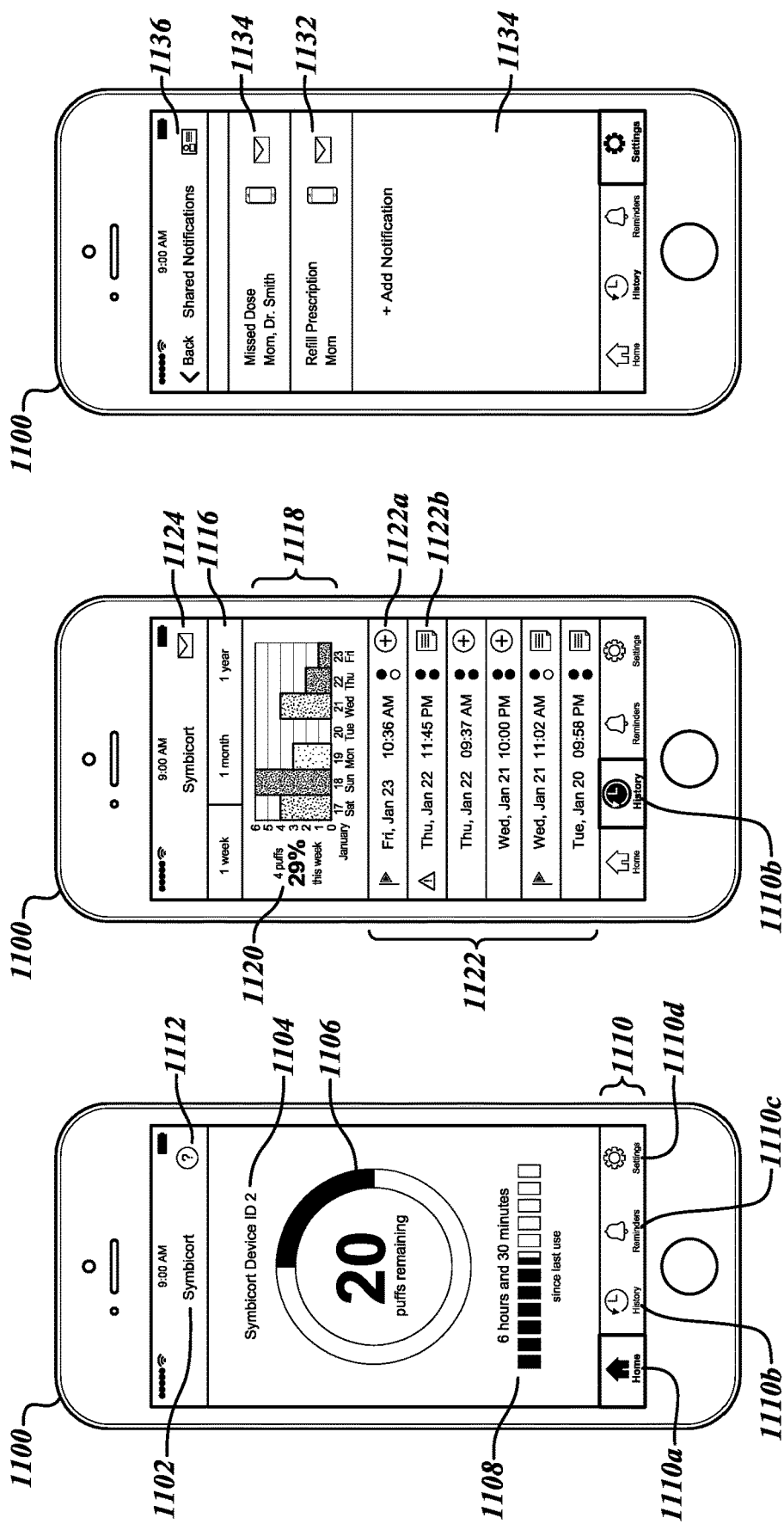

AEROSOL DELIVERY SYSTEMS AND RELATED METHODS

CROSS-REFERENCE TO RELATED APPLICATIONS

This application is a continuation of U.S. patent application Ser. No. 15/743,239, filed Jan. 9, 2018, which is a 371 of PCT/US2016/043004 filed Jul. 19, 2016, which claims the benefit of U.S. provisional application Nos. 62/194,701, filed Jul. 20, 2015, and 62/212,379, filed Aug. 31, 2015, the entire contents of which are hereby incorporated by reference herein.

BACKGROUND

Technical Field

This disclosure generally relates to aerosol delivery systems and related methods, and, more particularly, to aerosol delivery units suitable for selectively delivering a dose of aerosolized matter for inhalation by a user.

Description of the Related Art

It is well known to treat patients with medicaments contained in an aerosol, for example, in the treatment of respiratory disorders. It is also known to use for such treatment, medicaments which are contained in an aerosol and are administered to a patient by means of an inhalation device comprising a mouthpiece and a housing in which an aerosol canister is loaded. Such inhalation devices are generally referred to as metered dose inhalers (MDIs). The aerosol canisters used in such inhalation devices are designed to deliver a predetermined dose of medicament upon each actuation by means of an outlet valve member (e.g., metering slide valve) at one end which can be opened either by depressing the valve member while the canister is held stationary or by depressing the canister while the valve member is held stationary. In the use of such devices, the aerosol canister is placed in the housing with the outlet valve member of the canister communicating with the mouthpiece. When used for dispensing medicaments, for example, in bronchodilation therapy, the patient holds the housing in a more or less upright position and the mouthpiece of the inhalation device is placed in the mouth of the patient. The aerosol canister is manually actuated to dispense a dose of medicament from the canister which is then inhaled by the patient.

It may be understood that effective delivery of medicament to the patient using an inhalation device such as a conventional MDI is to an extent dependent on the patient's ability to manually actuate the device (e.g., discharging the aerosol) and to coordinate the actuation thereof with the taking of a sufficiently strong inward breath. For some patients, particularly young children, the elderly and the arthritic, manual actuation of the device can present difficulties. Other patients find it difficult to coordinate the taking of a reliable inward breath with actuation of the device. Thus, there is a risk of not receiving an appropriate dose of medicament. Conventional manually actuated MDIs also suffer from a variety of other deficiencies and drawbacks, including, for example, the ability to actuate the device while not in a generally upright position or without ensuring the medicament is sufficiently agitated within the container prior to delivery.

BRIEF SUMMARY

Embodiments described herein provide aerosol delivery systems and related methods particularly suitable for delivering a dose of aerosolized matter in an efficient and reliable manner for inhalation by a user. Embodiments include aerosol delivery systems featuring electronically controlled, motor-driven actuation of an aerosol canister which may be triggered by breath sensing techniques. Embodiments may be provided in multi-part form factors featuring a base housing including a motor-driven actuator and other system components, and a removable cartridge insertably receivable in the base housing to form a complete aerosol delivery unit for selectively delivering a dose of aerosolized matter to the user. Advantageously, the removable cartridge may be configured to enable manual actuation of the aerosol canister while removed from the main housing similar to a conventional MDI while providing enhanced functionality when received in the main housing.

Embodiments of the electronically controlled, motor-driven, breath actuated aerosol delivery systems described herein may provide enhanced user experience and may facilitate increased compliance by both simplifying the inhalation process and by providing targeted information to the user. To do this the aerosol delivery systems automate primary functions such as breath timing and canister actuation while also being instrumented to capture usage data which can be used to inform the user on correct inhalation technique. Information may be supplied to the user on board an aerosol delivery unit through a display screen, for example, through haptic and/or audible feedback and/or via an associated application running on a paired smart phone or other computing device with which the aerosol delivery unit may communicate wirelessly.

BRIEF DESCRIPTION OF THE SEVERAL VIEWS OF THE DRAWINGS

FIGS. 15A-15C depict certain portions of a Graphical User Interface (GUI) that may be provided via a client device communicatively coupled to an aerosol delivery unit in accordance with techniques and features described herein.

DETAILED DESCRIPTION

Figure 1:
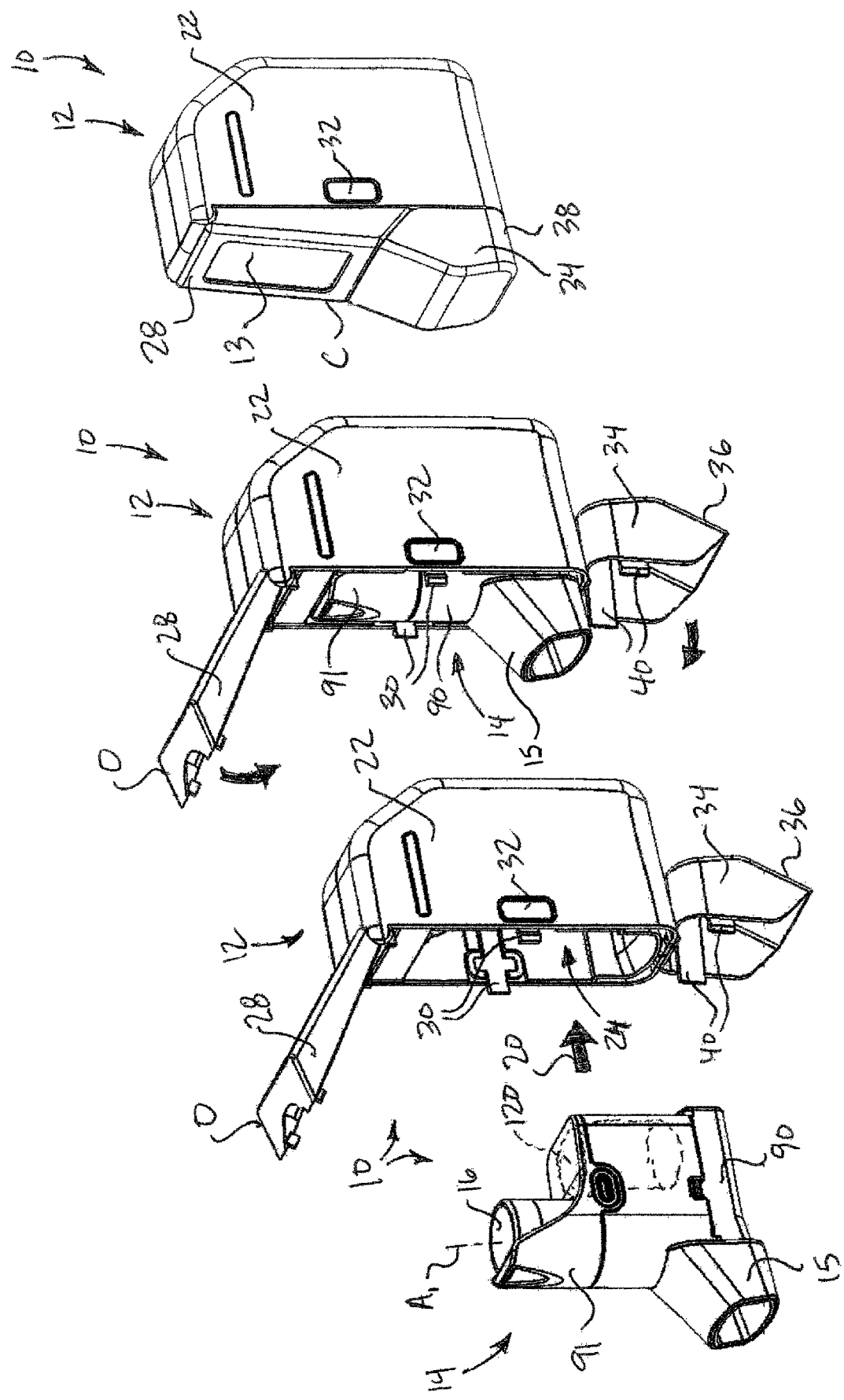
FIG. 1 is a skewed isometric view showing a sequence in which a removable cartridge containing an aerosol canister is inserted in a base housing to form an aerosol delivery unit, according to one embodiment.

In the following description, certain specific details are set forth in order to provide a thorough understanding of various disclosed embodiments. However, one of ordinary skill in the relevant art will recognize that embodiments may be practiced without one or more of these specific details. In other instances, well-known structures and devices associated with MDIs or other inhaler devices or components may not be shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Embodiments described herein provide aerosol delivery systems and related methods particularly suitable for delivering a dose of aerosolized matter in an efficient and reliable manner for inhalation by a user. Embodiments include aerosol delivery systems featuring electronically controlled, motor-driven actuation of an aerosol canister which may be triggered by breath sensing techniques. Embodiments may be provided in multi-part form factors featuring a base housing including the motor-driven actuator and other system components, and a removable cartridge containing an aerosol canister which may be insertably received in the base housing to form a complete aerosol delivery unit for selectively delivering a dose of aerosolized matter (e.g., medicament) to a user. Advantageously, the removable cartridge may be configured to enable manual actuation of the aerosol canister when removed from the main housing similar to a conventional MDI while providing enhanced functionality when received in the main housing. Other advantages will be appreciated from a detailed review of the present disclosure.

Although the aerosol delivery systems described herein are shown and described in the context of electronically controlled, motor-driven, breath actuated metered dose inhaler systems for delivering medicament or other aerosolized matter to a user, it will be appreciated by those of ordinary skill in the relevant art that features and aspects of such systems may applied to other devices and for other purposes.

FIG. 1 shows one example embodiment of an electronically controlled, motor-driven, breath actuated MDI in the form of an aerosol delivery unit 10. The aerosol delivery unit 10 includes a base housing 12, which includes a majority of the system electronics as described in more detail elsewhere, and a removable cartridge 14 that is removably coupleable to the base housing 12 for selectively delivering a dose of aerosolized matter (e.g., aerosolized medicament) to a user from an aerosol canister 16 carried by the removable cartridge 14.

With reference to FIG. 1, the example aerosol delivery unit 10 is a front loading device in which the removable cartridge 14 is insertable in the base housing 12 in a direction generally perpendicular to a longitudinal axis A1 of the aerosol canister 16 carried by the removable cartridge 14, as indicated by the arrow labeled 20. The base housing 12 may include a housing body 22 defining a cavity 24 within which the removable cartridge 14 may be received. An access door 28 may be rotatably coupled to the housing body 22 and may be movable between an open position O and a closed position C. In the open position O, the cavity 24 of the housing body 22 may be revealed for loading the cartridge 14 into the base housing 12, or for removing the cartridge 14 from the base housing 12. In the closed position C, the access door 28 may enclose the cartridge 14 within the cavity 24 of the base housing 12. One or more locking features 30 (e.g., resilient locking tabs, detents, latches) may be provided for securing the access door 28 to the housing body 22 in the closed position C, and one or more release devices 32 (e.g., push buttons) may be provided for releasing or unlocking the access door 28 such that it may move to the open position O. In other instances, the access door 28 may be opened by manually overcoming a threshold resistive force provided by the one or more locking features 30. In some instances, a bias member (e.g., torsional spring) may be provided to urge the access door 28 toward the open position O such that the access door 28 may move toward the open position O without manual assistance upon actuation of the one or more release devices 32 or upon overcoming the threshold resistive force.

With continued reference to FIG. 1, the base housing 12 may further include a mouthpiece cover 34 that is rotatably coupled to the housing to move between an open position 36 and a closed position 38. In the open position 36, the cavity 24 of the housing body 22 may be revealed for loading the cartridge 14 into the base housing 12 or for removing the cartridge 14 from the base housing 12. In the closed position 38, the mouthpiece cover 34 may conceal a mouthpiece 15 of the cartridge 14 received within the cavity 24 of the base housing 12. For this purpose, one or more locking features 40 (e.g., resilient locking tabs, detents, latches) may be provided for securing the mouthpiece cover 34 to the housing body 22 in the closed position 38. In some instances, one or more release devices (e.g., push buttons) may be provided for releasing or unlocking the mouthpiece cover 34 such that it may move to the open position 36. In other instances, the mouthpiece cover 34 may be opened by manually overcoming a threshold resistive force provided by the one or more locking features 40. In some instances, a bias member (e.g., torsional spring) may be provided to urge the mouthpiece cover 34 toward the open position 36 such that the mouthpiece cover 34 may move toward the open position 36 without manual assistance upon actuation of the one or more release devices or upon overcoming the threshold resistive force. The mouthpiece 15 may be removably coupled to the remainder of the removable cartridge 14 to facilitate cleaning or replacement of the mouthpiece 15. In some instances, for example, a separate removable mouthpiece 15 may be press fit or friction fit onto a corresponding mouthpiece receiving portion of the removable cartridge 14.

Figure 2:
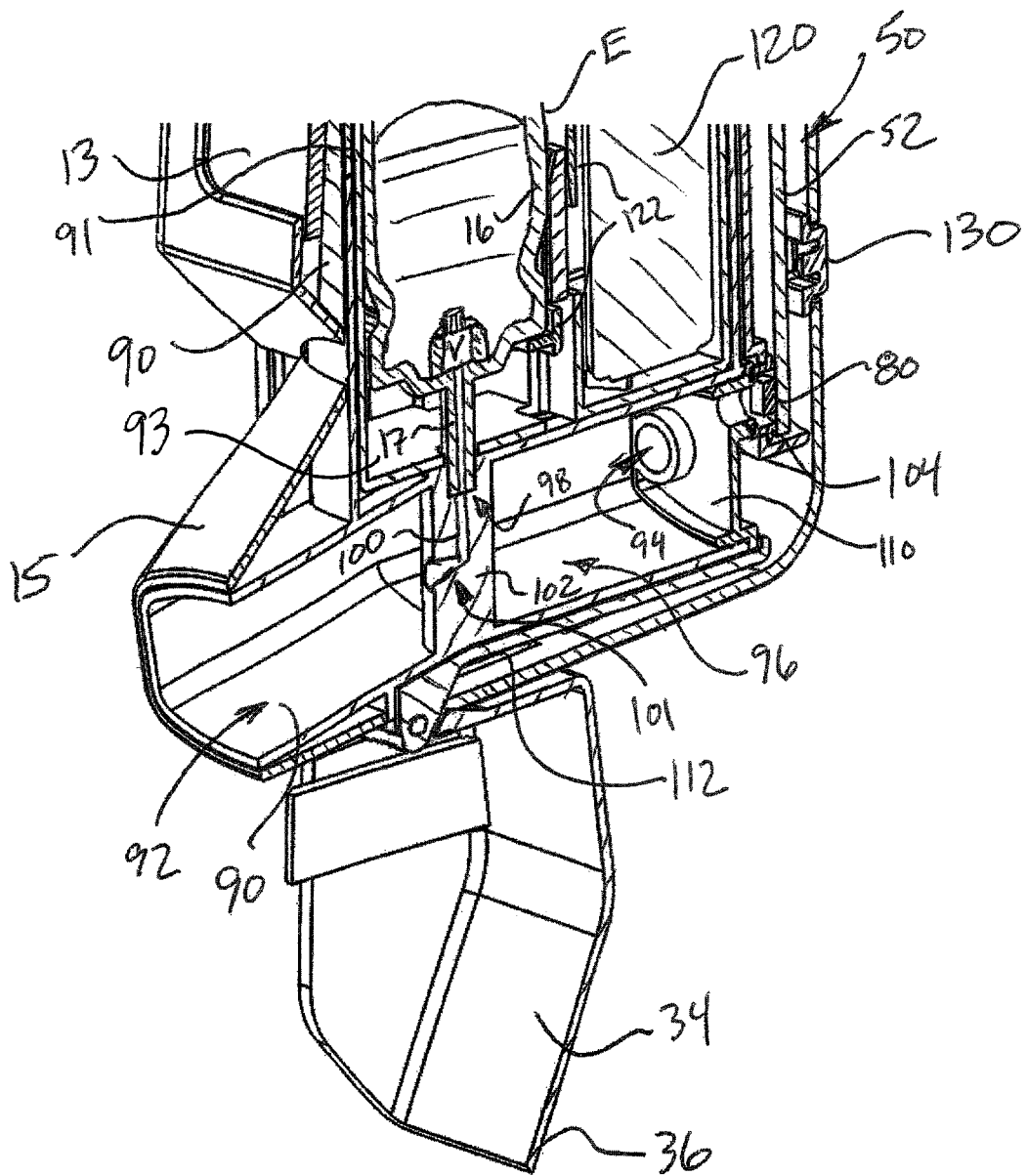
FIG. 2 is an enlarged partial cross-sectional view of the aerosol delivery unit of FIG. 1 shown with a mouthpiece cover open to reveal an outlet through which aerosolized matter is discharged for inhalation by a user.
Figure 3:
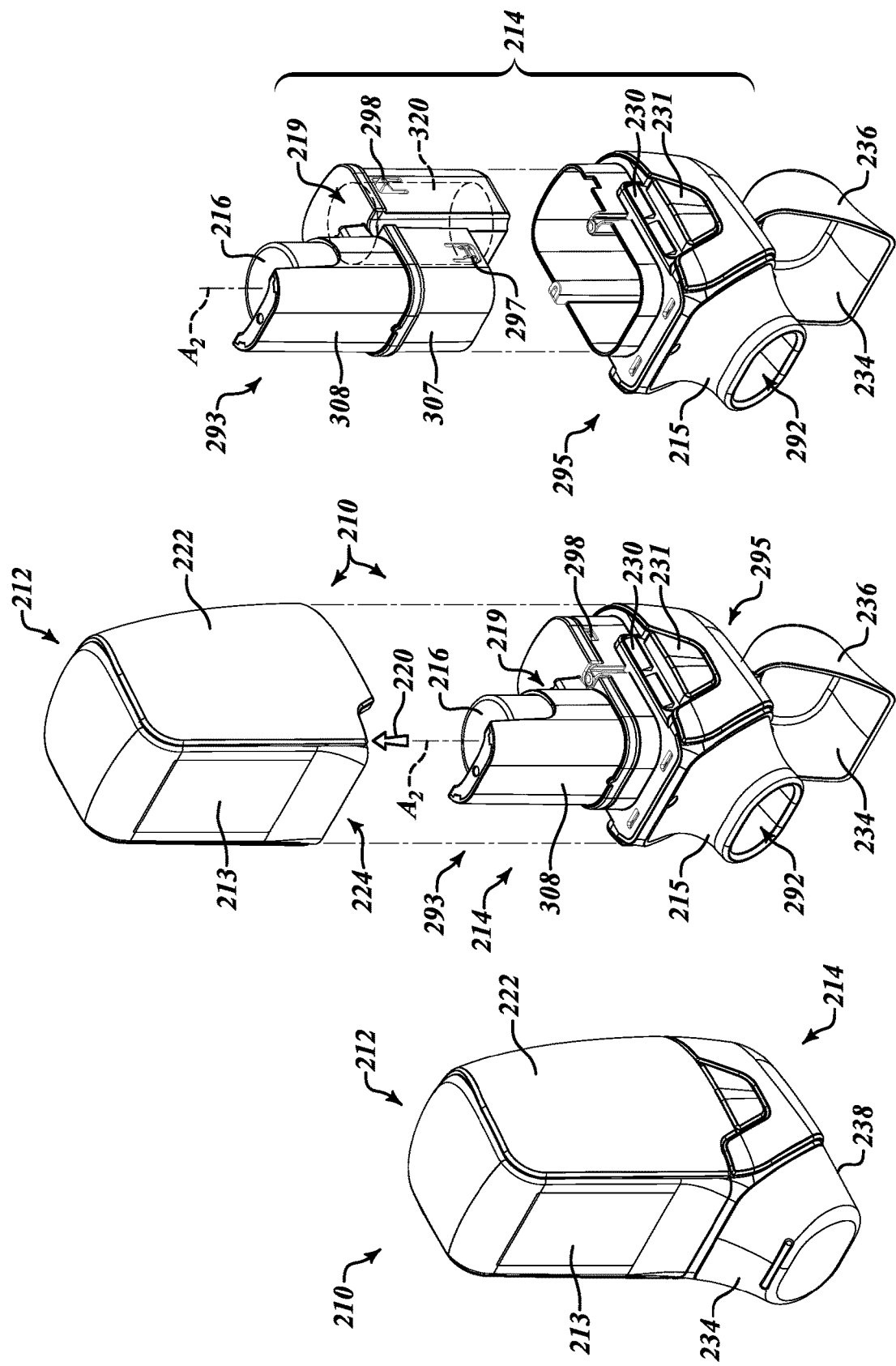
FIG. 3A is an isometric view of an aerosol delivery unit, according to another embodiment, which includes a removable cartridge coupled to a base housing.
FIG. 3B is an isometric view of the aerosol delivery unit of FIG. 3A with the removable cartridge shown separated from the base housing.
FIG. 3C is an isometric view of the removable cartridge portion of the aerosol delivery unit of FIG. 3A, which shows a canister chassis portion with an onboard power source separated from a mouthpiece subassembly.

FIG. 2 shows an enlarged cross-sectional portion of the aerosol delivery unit 10 for additional clarity.

According to the example embodiment shown in FIGS. 1 and 2, the complete aerosol delivery unit 10 may provide a portable or handheld unit capable of selectively delivering a dose of aerosolized matter with enhanced functionality, as described in more detail elsewhere.

FIGS. 3A through 9 show another example embodiment of an electronically controlled, motor-driven, breath actuated MDI in the form of an aerosol delivery unit 210. The aerosol delivery unit 210 includes a base housing 212, which includes a majority of the system electronics as described in more detail elsewhere, and a removable cartridge 214 that is removably coupleable to the base housing 212 for selectively delivering a dose of aerosolized matter (e.g., aerosolized medicament) to a user from an aerosol canister 216 carried by the removable cartridge 214.

With reference to FIGS. 3A-3C, the example aerosol delivery unit 210 is a bottom loading device in which the removable cartridge 214 is insertable in the base housing 212 in a direction generally parallel to a longitudinal axis A2 of the aerosol canister 216 carried by the removable cartridge 214, as indicated by the arrow labeled 220 in FIG. 3B. The base housing 212 may include a housing body 222 defining a cavity 224 within which the removable cartridge 214 may be insertably received. The housing body 222 may be a multi-piece assembly including, for example, an outer housing or cover and an inner base chassis to which other components may be attached. The aerosol delivery unit 210 may include one or more locking features 230 (e.g., resilient locking tabs, detents, latches) for securing the removable cartridge 214 to the base housing 212. In addition, one or more release devices 231 (e.g., push buttons) may be provided for releasing or unlocking the removable cartridge 214 from the base housing 212 such that it may be removed and replaced as needed or desired. In other instances, the removable cartridge 214 may be removed by manually overcoming a threshold resistive force provided by the one or more locking features. In some instances, a bias member (e.g., leaf spring) may be provided to assist in driving the removable cartridge 214 away from the base housing 212 upon actuation of the one or more release devices 231 or upon overcoming the threshold resistive force.

With continued reference to FIGS. 3A-3C, the removable cartridge 214 may further include a mouthpiece cover 234 that is rotatably coupled to surrounding structures to move between an open position 236, as shown in FIGS. 3B and 3C, and a closed position 238, as shown in FIG. 3A. In the closed position 238, the mouthpiece cover 234 conceals a mouthpiece 215 of the cartridge 214. In the open position 236, the mouthpiece 215 is revealed for use. For this purpose, one or more locking features (e.g., resilient locking tabs, detents, latches) may be provided for securing the mouthpiece cover 234 in the closed position 238. In some instances, one or more release devices (e.g., push buttons) may be provided for releasing or unlocking the mouthpiece cover 234 such that it may move to the open position 236. In other instances, the mouthpiece cover 234 may be opened by manually overcoming a threshold resistive force provided by the one or more locking features. In some instances, a bias member (e.g., torsional spring) may be provided to urge the mouthpiece cover 234 toward the open position 236 such that the mouthpiece cover 234 may move toward the open position 236 without manual assistance upon actuation of the one or more release devices or upon overcoming the threshold resistive force. The mouthpiece 215 may be removably coupled to other portions of the removable cartridge 214 to facilitate cleaning or replacement of the mouthpiece 215. In some instances, for example, a separate removable mouthpiece 215 may be press fit or friction fit onto a corresponding mouthpiece receiving portion of the removable cartridge 214.

Advantageously, when the mouthpiece cover 234 is in the open position 236, the mouthpiece cover 234 may hinder or prevent a user from inadvertently covering unit intake apertures 312 (FIG. 9) provided at the bottom of the aerosol delivery unit 210 for enabling air to enter the unit 210 to assist in delivering the aerosolized matter.

With reference to FIG. 3C, the removable cartridge 214 may be provided in separable portions. For example, the removable cartridge 214 may include a canister chassis 293 and a mouthpiece subassembly 295 that is configured to removably receive the canister chassis 293. The canister chassis 293 is structured to accommodate, among other things, the canister 216 and an onboard power source 320, as discussed in more detail elsewhere. The mouthpiece assembly 295 includes, among other things, the mouthpiece 215 and a stem support 302 (FIGS. 4 and 5) for receiving the valve stem 217 of the canister 216 and supporting the canister 216 in fluid communication with the mouthpiece 215, as discussed in more detail elsewhere. The canister chassis 293 is removably coupleable to the mouthpiece subassembly 295 to form a fully functional, manually depressible cartridge that includes functionality similar to that of a conventional manually depressible MDI. In this manner, a user can optionally use the removable cartridge 214 as a suitable inhaler device without the added functionality provided when coupling the removable cartridge 214 to the base housing 212. The canister chassis 293 may be removably coupleable to the mouthpiece subassembly 295 via one or more fastening devices or techniques, including for example, one or more detent mechanisms 297 provided on the canister chassis 293 that are arranged to engage corresponding features (not visible) of the mouthpiece subassembly 295.

Figure 4:
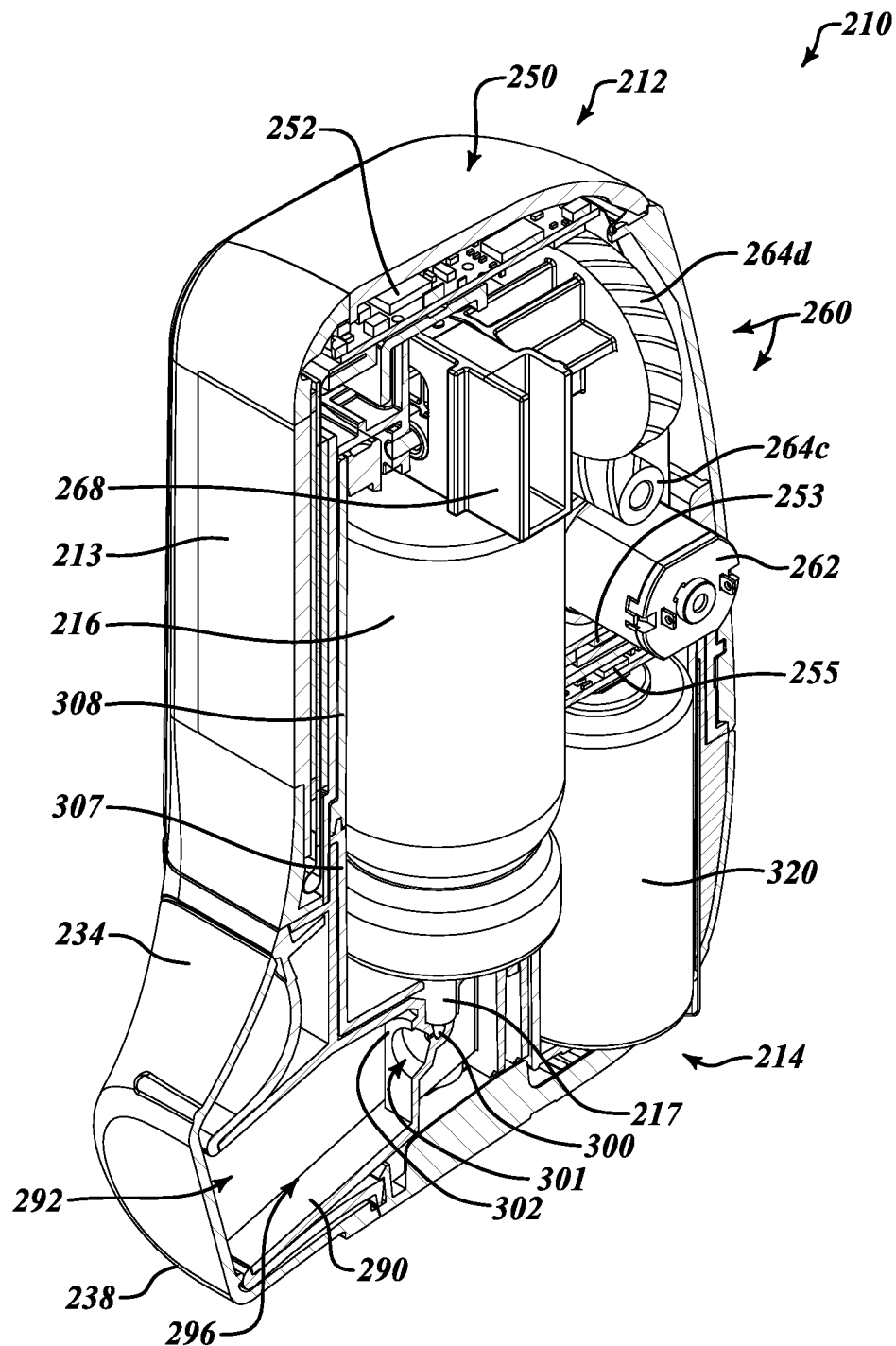
FIG. 4 is an isometric cross-sectional view of the complete aerosol delivery unit shown in FIG. 3A from one perspective.
Figure 5:
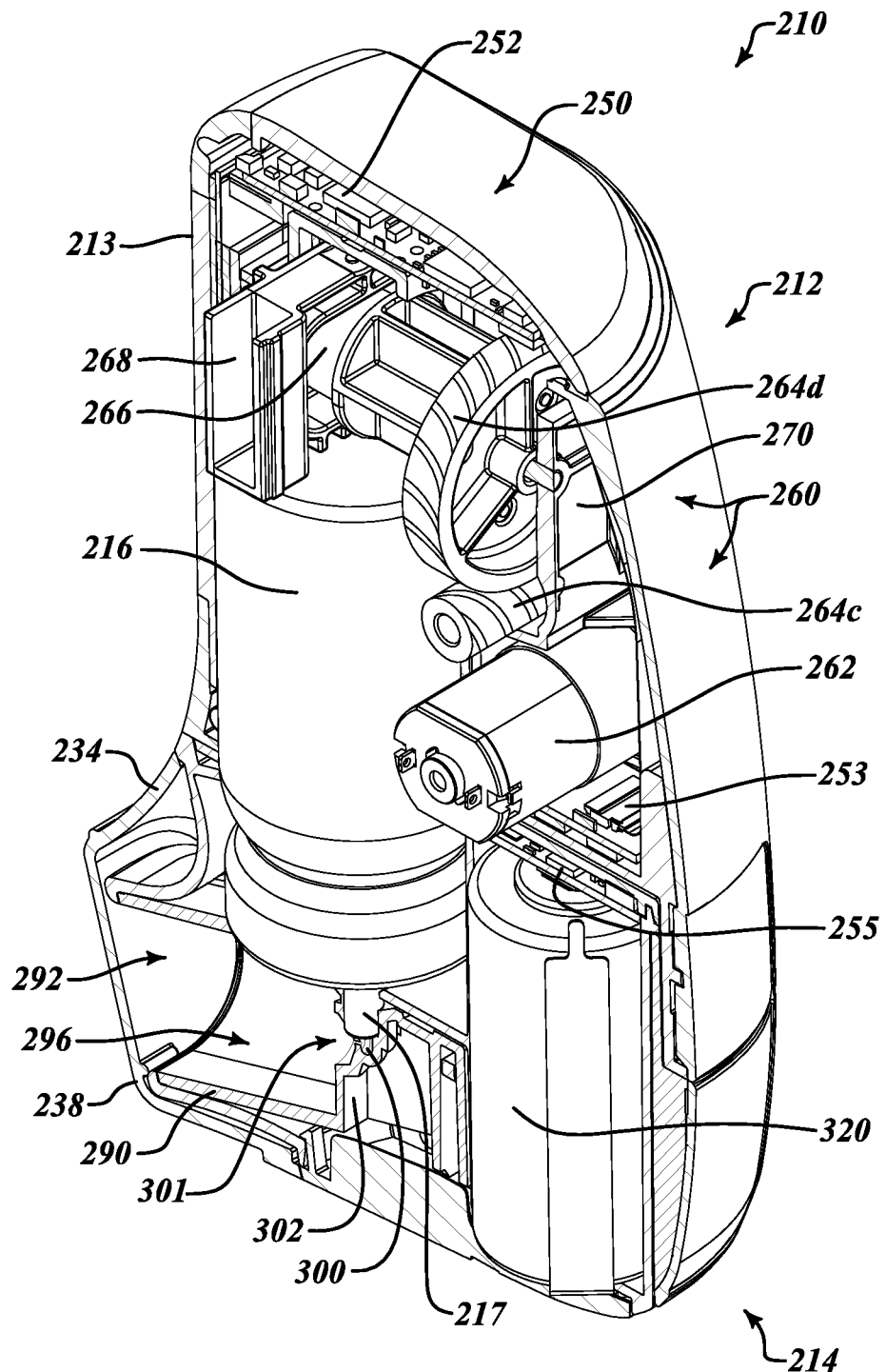
FIG. 5 is an isometric cross-sectional view of the complete aerosol delivery unit shown in FIG. 3A from another perspective.

FIGS. 4 and 5 provide cross-sectional views of the complete aerosol delivery unit 210 from different viewpoints with the removable cartridge 214 coupled to the base housing 212 so as to reveal various internal components of the aerosol delivery unit 210 which are configured to provide, among other functionality, electronically controlled, motor-driven, breath actuated, metered dose delivery of aerosolized matter to a user.

Figure 6:
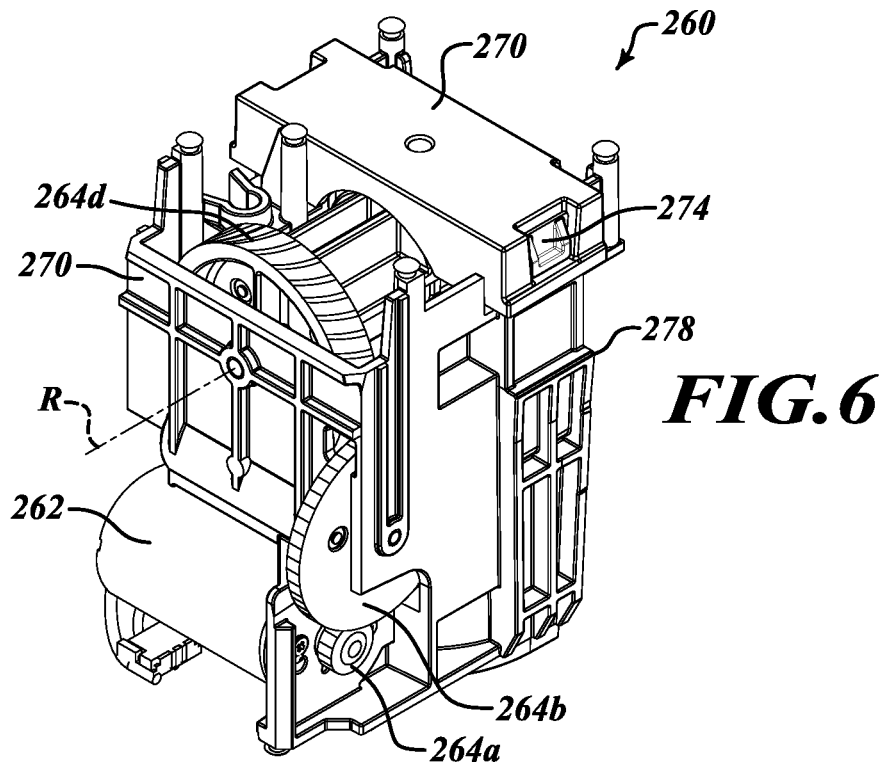
FIG. 6 is an isometric view of a motor-driven actuator assembly of the aerosol delivery unit of FIG. 3A.
Figure 7:
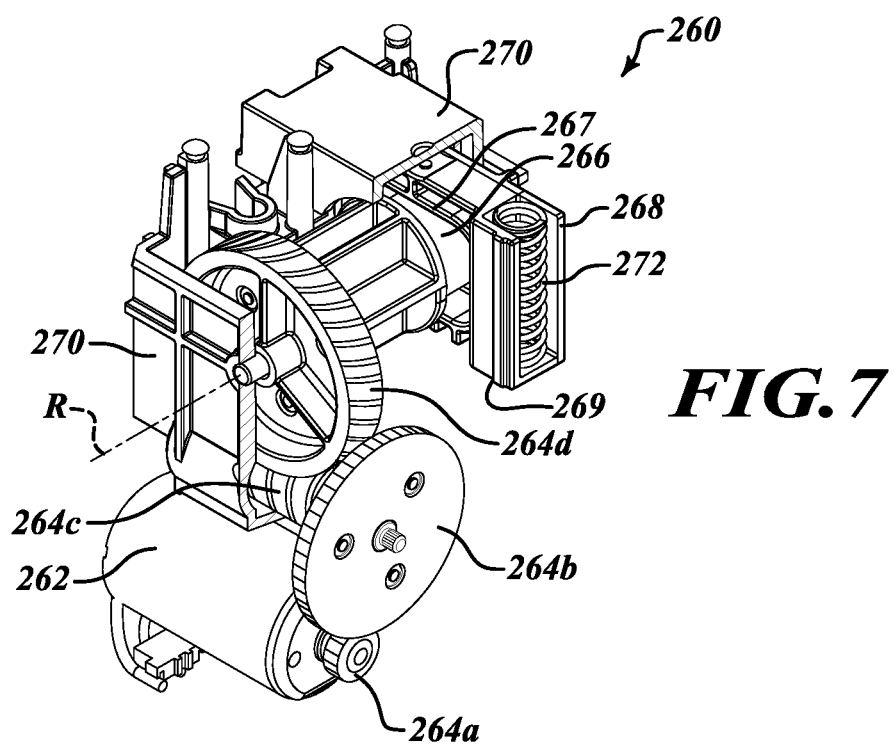
FIG. 7 is an isometric view of the motor-driven actuator assembly of FIG. 6 with the casing partially removed to reveal internal components thereof.
Figure 8:
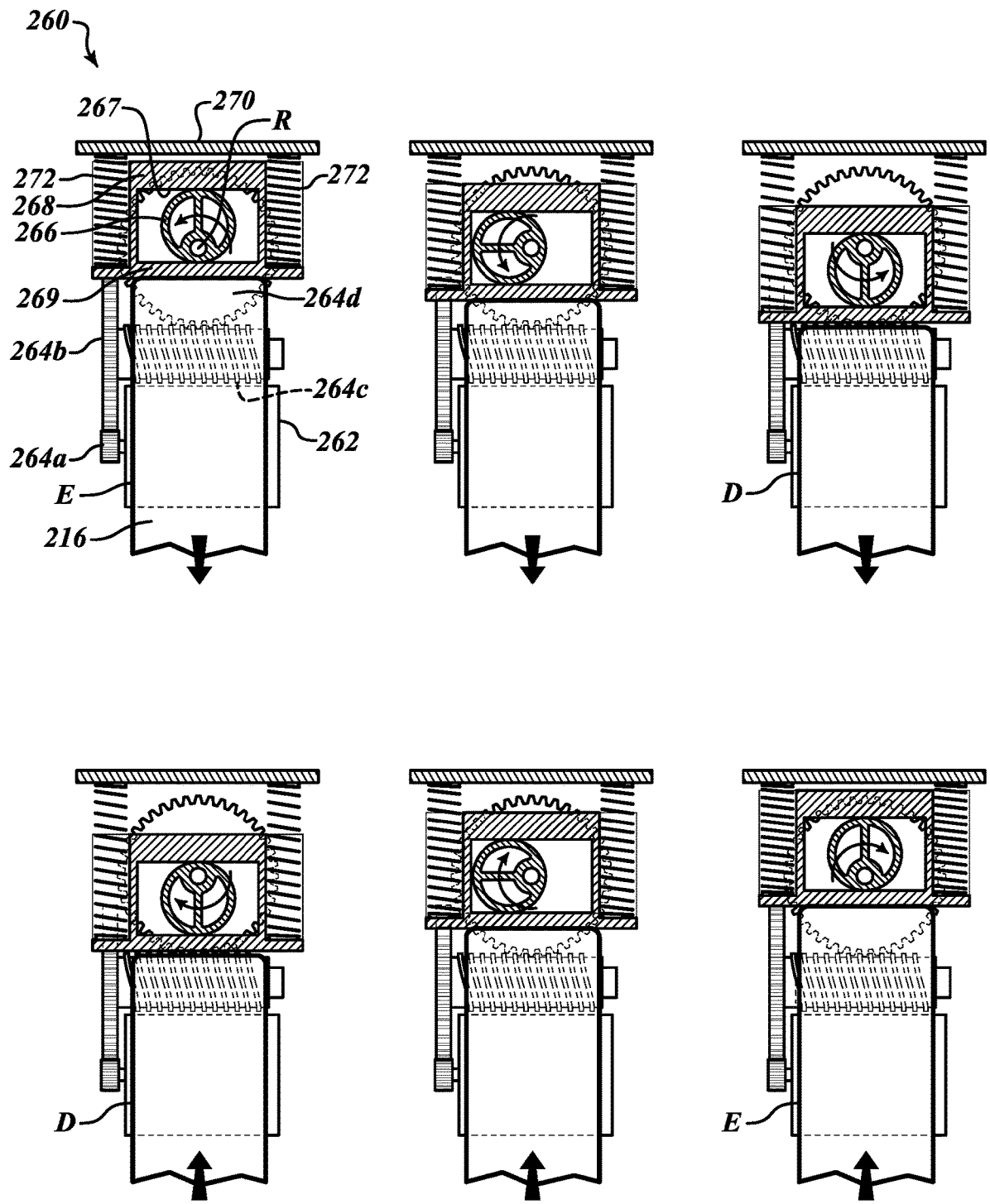
FIG. 8 is diagram illustrating actuation of the aerosol canister via the motor-driven actuator assembly of FIGS. 6 and 7.

The base housing 212 is provided with, among other features, a control system 250, including a main printed circuit board (PCB) 252 and a sub PCB 253, and an actuator assembly 260 electronically coupled to the PCBs 252, 253 for providing controlled actuation of the aerosol canister 216. Further details of the actuator assembly 260 are shown in FIGS. 6 through 8. More particularly, FIGS. 6 and 7 show the actuator assembly 260 isolated from all other system components for clarity and FIG. 8 provides a diagram showing actuation of the aerosol canister 216 via the actuator assembly 260 between an expanded configuration E, in which a valve member of the aerosol canister 216 remains closed, and a depressed configuration D, in which the valve member of the aerosol canister 216 transitions to an open position to release a metered dose of aerosolized matter.

With reference to FIGS. 6 and 7, the actuator assembly 260 includes an electric motor 262 (e.g., DC electric motor), a gear train 264a-264d, a cam member 266 and a yoke 268 that is driven by the cam member 266 via the electric motor 262 and the gear train 264a-264d. The electric motor 262, the gear train 264a-264d, the cam member 266 and the yoke 268 may be partially enclosed in a casing 170, as shown in FIGS. 6 and 7, substantially enclosed in a casing, or fully enclosed in a casing. Bias members 272 in the form of compression springs are provided between the yoke 268 and the casing 270 for urging the yoke 268 into contact with the cam member 266 and providing mechanical assistance in moving the aerosol canister 216 from the expanded configuration E to the depressed configuration D as the cam member 266 is driven to rotate about an axis of rotation R by the electric motor 262 and gear train 264a-264d. The casing 270 may include a plurality of separate casing portions and may be coupled together by corresponding coupling features 274 (e.g., snaps, detents, latches) to partially, substantially, or completely enclose the electric motor 262, the gear train 264a-264d, the cam member 266 and the yoke 268. The casing 270 includes at least one opening through which a lower end 269 of the yoke 268 extends to contact the aerosol canister 216 during actuation.

During actuation, the electric motor 262 is driven by the control system 250 in response to a trigger signal to move the canister 216 through the sequence illustrated in FIG. 8 to compress and release the aerosol canister 216 to discharge a dose of the aerosol matter for inhalation by a user. More particularly, as will be appreciated from a review of FIG. 8, the cam member 266 is controlled to rotate in direct correlation with rotation of the electric motor 262 via the gear train 264a-264d and to ride in a slot 267 of the yoke 268 and bear against the yoke 268 to urge the yoke 268 downward into contact with the canister 216 during a downward stroke (i.e., valve opening stroke) to push the canister to the depressed configuration D and to thereafter enable the yoke 268 to move back upward during a return stroke (i.e., valve closing stroke) to enable the canister 216 to return to the expanded configuration E under the force of an internal bias member (e.g., valve spring) of the canister 216. In this manner, the position of the yoke 268 and hence canister 216 may be precisely controlled by the electric motor 262 and other components of the control system 250.

With reference to FIGS. 6 and 7, the gear train 264a-264d may include a drive spur gear 264a coupled directly to a drive shaft of the electric motor 262, a driven spur gear 264b meshed with the drive spur gear 264a, a worm screw 264c formed integrally with the driven spur gear 264b to rotate in unison therewith, and a worm wheel 264d meshed with the worm screw 264c. The worm screw 264c and the worm wheel 264d may form a worm gear set or worm drive portion of the gear train 264a-264d, and may include a 2 start worm. According to some embodiments, including the example embodiment of the actuator assembly 260 shown in FIGS. 6 and 7, the gear ratio of the driven spur gear 264b and the drive spur gear 264a may be at least 2:1 and the worm drive may comprise a 2 start worm with a gear ration of at least 20:1 to provide increased torque for actuating the aerosol canister 216.

According to the illustrated embodiment, the worm screw 264c has an axis of rotation parallel to an axis of rotation of the electric motor 262 and the worm wheel 264d is meshed with the worm screw 264c to rotate perpendicular thereto. In some instances, the cam member 266 and the worm wheel 264d may be portions of the same unitary part such that a rotational position of the electric motor 262 controls the rotational position of the cam member 266 via the intermediary of the driven spur gear 264b and the worm gear set 264c, 264d. During actuation, and as previously described, the cam member 266 rides in the slot 267 of the yoke 268 and bears against the yoke 268 to urge the yoke 268 downward into contact with the canister 216 during a downward stroke to move the canister 216 into the depressed configuration D and to thereafter enable the yoke 268 to move back upward during a return stroke to enable the canister 216 to return to the expanded configuration E under the force of an internal bias member of the canister 216.

More particularly, as the motor 262 drives in a forward direction, the yoke 268 moves linearly downward and depresses the canister 216. Since the canister valve stem 217 is fixed in the stem support 302 (FIGS. 4 and 5), the valve stem 217 is compressed. The yoke 268 continues to depress the canister 216 until the motor 262 reaches its stall torque. The motor 262 may stall under three conditions: (i) the canister valve spring force balances the motor torque via the gear-train 264a-264d; (ii) the canister valve stem bottoms-out; or (iii) the worm-wheel 264d reaches a forward end stop. In any of these cases, the system is designed such that the valve stem 217 will be compressed beyond its firing point before the stall torque is reached.

In order to prevent the motor 262 from wasting power and overheating when it is stalled (e.g., due to the canister 216 reaching the end-stop during actuation or due to the motor 262 otherwise reaching its stall torque), the control system 250 may monitor feedback signals from the motor control electronics which exhibit distinct patterns when the motor 262 is running or stalled. Once stall is detected, forward drive power to the motor 262 is cut. The control system 250 may then wait for a dwell-time sufficient to ensure that the matter delivered by through the valve stem 217 has time to vaporize and enter the inhalation passageway 296. The motor 262 is then driven in the reverse direction until it stalls on a worm-wheel home position end stop. A canister valve spring causes the canister 216 to return to its normal position, allowing the metering valve to refill in readiness for a subsequent dose.

Advantageously, in some embodiments, the entire gear train 264a-264d, the cam member 266 and the yoke 268 may be injection molded plastic components and may be supported without separate bearings (e.g., roller bearings). In this manner, the weight of the actuator assembly 260 may be minimized and the complexity of the assembly reduced. Overall, the actuator assembly 260 shown in FIGS. 6 and 7 provides a particularly lightweight yet durable drive system for electronic controlled actuation of the aerosol canister 216, which is particularly advantageous for providing a handheld or portable aerosol delivery unit 210.

With reference again to FIGS. 4 and 5, the actuator assembly 260 may be provided in an upper portion of the base housing 212 to interface with an upper end of the aerosol canister 216 when the removable cartridge 214 is installed for use. The casing 270 of the actuator assembly 60 may include one or more coupling features 278 (FIG. 6) for engaging the base housing 212 or a chassis thereof. The electric motor 262 of the actuator assembly 260 is communicatively coupled to the PCBs 252, 253 of the control system 250 for controlling motion of the electric motor 262 and hence actuation of the aerosol canister 216.

In some instances, the actuator assembly 260 may be controlled to actuate the aerosol canister 216 in response to a pressure signal arising from inhalation of a user via a mouthpiece 215 of the removable cartridge 214. For this purpose, the control system 250 may further include a pressure sensor 280 (e.g., a microelectromechanical systems (MEMS) pressure sensor) communicatively coupled to the main PCB 252. In some instances, the pressure sensor 280 may be coupled directly to the main PCB 252 and may be positioned to interface with the removable cartridge 214 to sense a change in pressure within the removable cartridge 214 arising from inhalation by a user in order to trigger actuation of the aerosol canister 216. The pressure sensor 280 may further include temperature sensing functionality or otherwise operate in conjunction with a separate temperature sensor to provide pressure and temperature data for calculating the air flow rate through the unit 210 from which to trigger the actuation of the aerosol canister 216.

For instance, with reference to the enlarged cross-sectional view of FIG. 2 from the example embodiment of the aerosol delivery unit 10 shown in FIG. 1, the removable cartridge 14 may include a cartridge body 90 having a mouthpiece aperture 92 through which to inhale aerosolized matter released from the canister 16, one or more inhalation passageway intake apertures or orifices 94 through which air can enter, and an inhalation passageway 96 extending from a location of the one or more inhalation passageway intake apertures or orifices 94 to a location of the mouthpiece aperture 92, the inhalation passageway 96 being in fluid communication with a discharge outlet 98 of the aerosol canister 16. More particularly, the inhalation passageway 96 may be in fluid communication with the discharge outlet 98 of the aerosol canister 16 via a discharge passageway 100 extending through a stem support 102 of the cartridge body 90 within which a stem 17 of the canister 16 is received. The discharge passageway 100 may terminate in an outlet 101 that is generally aligned with the inhalation passageway 96 such that the discharged aerosolized matter may be effectively withdrawn from the cartridge 14 with the same inhalation breath that triggers its release.

The pressure sensor 80 may be arranged to detect pressure within the inhalation passageway 96 near the one or more inhalation passageway intake apertures or orifices 94, with a change in the pressure being indicative of one or more characteristics of a flow of air moving through the one or more inhalation passageway intake apertures or orifices 94. A compliant seal 104 may be positioned around the pressure sensor 80 to engage the removable cartridge 14 and provide a sealed passageway 106 extending from the pressure sensor 80 toward the inhalation passageway 96 of the removable cartridge 14. In this manner, during inhalation, air may enter the inhalation passageway 96 only through the one or more inhalation passageway intake apertures or orifices 94 to subsequently pass through the inhalation passageway 96 wherein the aerosolized matter is mixed with the air stream and withdrawn from the mouthpiece aperture 92 by the user.

With continued reference to FIG. 2, the cartridge body 90 may define at least a majority of the inhalation passageway 96 and an orifice plate 110 including the one or more inhalation passageway intake apertures or orifices 94 may be coupled to an intake end of the cartridge body 90. In a particularly advantageous embodiment, the orifice plate 110 may consist of a respective orifice 94 positioned on each of opposing sides of the aerosol delivery unit 10 and the pressure sensor 80 may be located centrally between the orifices 94. As an example, the orifice plate 110 shown in FIG. 2 may be symmetrically formed about a central plane bisecting the aerosol delivery unit 10 such that a respective orifice 94 is positioned on each of opposing sides of the aerosol delivery unit 10, and the pressure sensor 80 may be located at or near the central plane. The orifices 94 may be the same size and may collectively define or establish a relationship between the sensed pressure and one or more characteristics of a flow of air moving therethrough from which to then control the release of the aerosolized matter. The size and shape of the orifices 94 may be determined in accordance with the capabilities of the pressure sensor 80 to provide a suitable pressure profile throughout inhalation from which to determine when a threshold airflow is exceeded for controlling the delivery of the aerosolized matter.

Although the inhalation passageway intake apertures or orifices 94 of the illustrated embodiment include two relatively small apertures having a circular cross-sectional profile and being positioned immediately adjacent a respective sidewall of the cartridge body 90 that defines the inhalation passageway 96, it is appreciated that the number, size, shape and position of the inhalation passageway intake apertures or orifices 94 may vary. For example, one, three, four or more inhalation passageway intake orifices 94 may be provided and the orifice(s) may have an oblong or other regular or irregular cross-sectional shape. In addition, although the one or more inhalation passageway intake apertures or orifices 94 are shown as being provided in a separate orifice plate 110 coupled to an intake end of the cartridge body 90, it is appreciated that in some instances the one or more intake apertures or orifices 94 may be provided directly in the cartridge body 90. For example, in some embodiments, the orifice plate 110 may be an integral portion of the cartridge body 90, rather than a separate component. The housing body 22 of the base housing 12 which surrounds the removable cartridge 14 during motor-driven, breath actuated use of the aerosol delivery unit 10 may include one or more unit intake apertures 112 for enabling external air to infiltrate the housing body 22 before moving through the inhalation passageway intake apertures or orifices 94 provided in the inhalation passageway 96 of the removable cartridge 14, which, apart from the inhalation passageway intake apertures or orifices 94 and mouthpiece aperture 92, is otherwise sealed.

Figure 9:
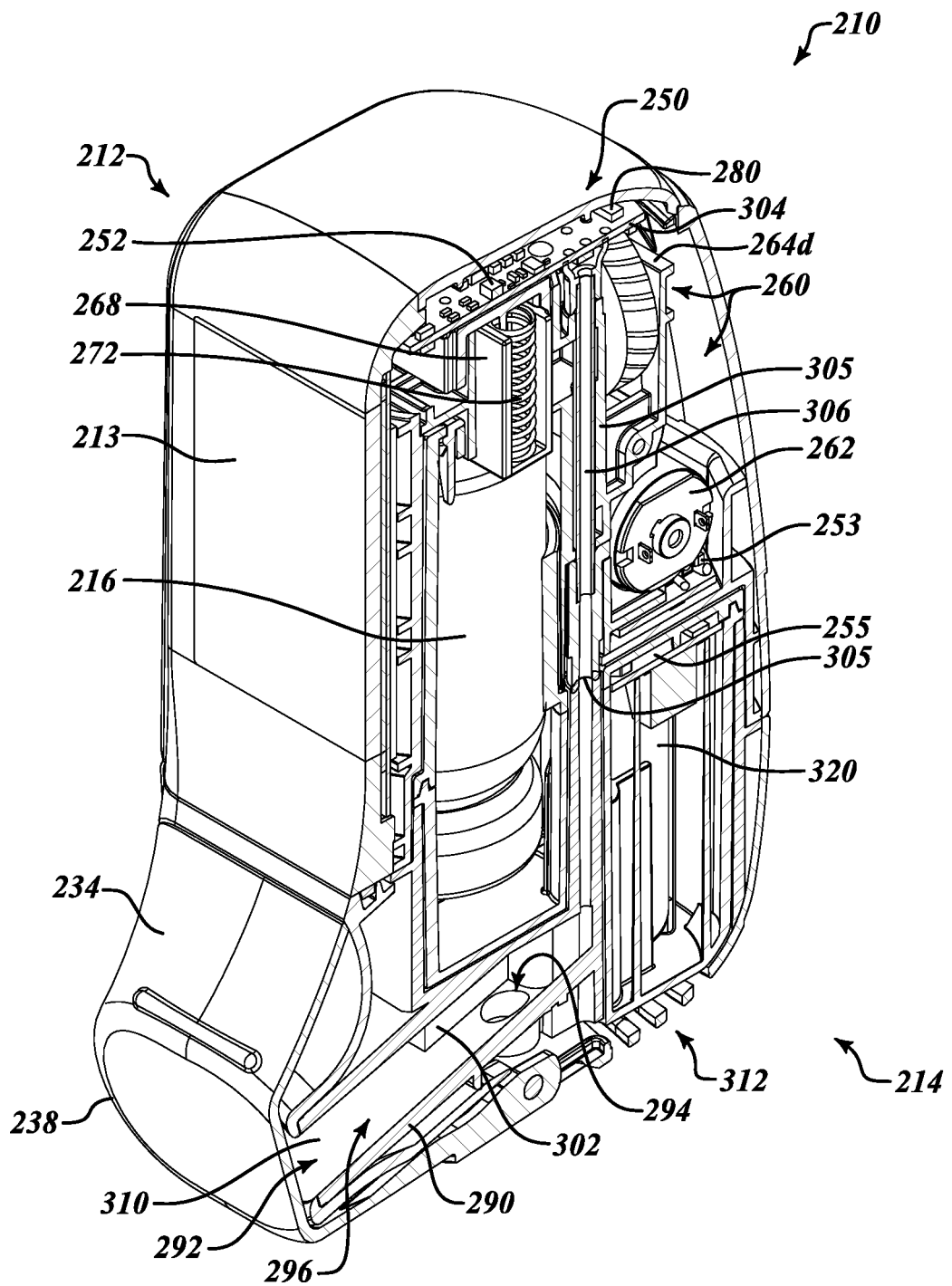
FIG. 9 is a cross-sectional view of the aerosol delivery unit of FIG. 3A showing a pressure sensor within the base housing which is in communication with the inhalation passageway of the removable cartridge to sense an inhalation event and trigger actuation of the canister.

As another example, and with reference to the cross-sectional views of FIGS. 4, 5 and 9 from the example embodiment of the aerosol unit 210 of FIGS. 3A-3C, the removable cartridge 214 may include a cartridge body 290 having a mouthpiece aperture through which to inhale aerosolized matter released from the canister 216, one or more inhalation passageway intake apertures or orifices 294 through which air can enter, and an inhalation passageway 296 extending from a location of the one or more inhalation passageway apertures or orifices 294 to a location of the mouthpiece aperture 292, the inhalation passageway 296 being in fluid communication with a discharge outlet of the aerosol canister 216. More particularly, with reference to FIGS. 4 and 5, the inhalation passageway 296 may be in fluid communication with the discharge outlet of the aerosol canister 216 via a discharge passageway 300 extending through a stem support 302 of the cartridge body 290 within which a stem 217 of the canister 216 is received. The discharge passageway 300 may terminate in an outlet 301 that is generally aligned with the inhalation passageway 296 such that the discharged aerosolized matter may be effectively withdrawn from the cartridge 214 with the same inhalation breath that triggers its release.

With reference to FIG. 9, the pressure sensor 280 may be arranged to detect pressure within the inhalation passageway 296 in the vicinity of the one or more inhalation passageway intake apertures or orifices 294, with a change in the pressure being indicative of one or more characteristics of a flow of air moving through the one or more inhalation passageway intake apertures or orifices 294. For this purpose, a pressure sensing conduit 303 may extend through the unit 210 from a vicinity of the one or more inhalation passageway intake apertures 294 in the cartridge body 290 to the pressure sensor 280, which may be mounted on the main PCB 252 in the base housing 212. In addition, compliant seals 304, 305 may be positioned around the pressure sensor 280 and at an interface between a base housing portion of the pressure sensing conduit 303 and a removable cartridge portion of the pressure sensing conduit 303 to provide a sealed passageway 306 that extends from the pressure sensor 280 toward the inhalation passageway 296 within the removable cartridge 214. In this manner, during inhalation, air may enter the inhalation passageway 296 only through the one or more inhalation passageway intake apertures or orifices 294 to subsequently pass through the inhalation passageway 296 wherein the aerosolized matter is mixed with the air stream and withdrawn from the mouthpiece aperture 292 by the user.

With continued reference to FIG. 9, the cartridge body 290 may define at least a majority of the inhalation passageway 296 and the one or more cartridge intake apertures or orifices 294 may be formed in a floor portion 310 thereof. In a particularly advantageous embodiment, the cartridge body 290 may include a respective orifice 294 positioned on each of opposing sides of the aerosol delivery unit 210, and more particularly on each of opposing sides of the stem support 302. The orifices 294 may be the same size and may collectively define or establish a relationship between the sensed pressure and one or more characteristics of a flow of air moving therethrough from which to then control the release of the aerosolized matter. The size and shape of the orifices 294 may be determined in accordance with the capabilities of the pressure sensor 280 to provide a suitable pressure profile throughout inhalation from which to determine when a threshold airflow is exceeded for controlling the delivery of the aerosolized matter.

Although the inhalation passageway apertures or orifices 294 of the illustrated embodiment include two relatively small apertures having a circular cross-sectional profile which are positioned on opposing sides of the stem support 302, it is appreciated that the number, size, shape and position of the cartridge intake apertures or orifices 294 may vary. For example, one, three, four or more intake orifices 294 may be provided and the orifice(s) may have an oblong or other regular or irregular cross-sectional shape.

As shown in FIG. 9, the removable cartridge 214 of the aerosol delivery unit 210 may include one or more unit intake apertures 312 (such as may from an intake grate) for enabling external air to infiltrate a portion of the aerosol delivery unit 210 before moving through the inhalation passageway intake apertures or orifices 294 provided in the inhalation passageway 296, which, apart from the inhalation passageway intake apertures or orifices 294 and mouthpiece aperture 292, is otherwise sealed.

With reference back to FIGS. 1 and 2, the removable cartridge 14 may include the cartridge body 90 and one or more additional body portions, such as a cartridge cap 91, coupleable together to retain the aerosol canister 16 and other components within the removable cartridge 14. Advantageously, the other components may include a power source 120 having sufficient capacity to power an actuator assembly for depressing the canister and other electronic components of the aerosol delivery unit 10 throughout the usable life of the aerosol canister 16 (i.e., until the aerosol canister 16 is depleted). In this manner, a new power source 120 may be provided with each new removable cartridge 14 to ensure sufficient power capacity to power the aerosol delivery unit 10 without interruption. In other words, a new replacement cartridge 14 may be supplied periodically with a new medicament canister 16 and a new power source 120 (e.g., battery) to provide prolonged treatment in a safe and effective manner.

In some embodiments, the aerosol canister 16 and the power source 120 may be accommodated in adjacent compartments of the removable cartridge 14. In other embodiments, the aerosol canister 16 and the power source 120 may be provided in the same compartment. In some instances, the power source 120 may be shaped to conform around at least a portion of the canister 16 to provide additional space savings and to reduce the overall form factor of the aerosol delivery unit 10.

The removable cartridge 14 may comprise electrical contacts (not visible), such as on a rear end of the cartridge 14 for providing power from the power source 120 carried onboard the cartridge 14 to the actuator assembly (not visible) and other system components provided in the base housing 12 when the cartridge 14 is coupled to the base housing 12 for use. A supplemental PCB (not visible) may be provided in the removable cartridge 14 and may be in electrical communication with the power source 120 and the aforementioned electrical contacts.

Although the removable cartridge 14 of the example embodiment of the aerosol delivery unit 10 shown in FIGS. 1 and 2 preferably includes an onboard power source 120 sufficient to power all electronic components of the aerosol delivery unit 10 throughout the usable life of the cartridge 14, in some instances the removable cartridge 14 may lack a power source altogether, or in other instances, may include a low capacity power source sufficient only to provide power for some limited functionality, such as, for example, maintaining an accurate dose count associated with the canister 16. In such instances, a suitable power source, including a replaceable power source or rechargeable power source, may be provided in or integrated with the base housing 12 and the size of the removable cartridge 14 may be reduced to provide a particularly slender or low profile cartridge. For embodiments featuring a rechargeable power source, a separate docking unit or station may be provided for selectively charging the rechargeable power source within the base housing 12.

With reference to FIGS. 1 and 2, a dose counter arrangement, including a depressible carriage 122 and a counter switch (not visible), may be provided within the removable cartridge 14 so as to count and track the number of doses administered and/or remaining in the removable cartridge 14. The dose counter arrangement may be electrically coupled to the supplemental PCB and a storage device (e.g., non-volatile memory) integrated in the supplemental PCB for storing dose information and optionally communicating the dose information to other portions of a control system, including, for example, a main PCB provided in the base housing 12. One or more additional switches may also be provided for ensuring that a dose count is valid only when the system is properly assembled. For example, a chassis 93 carrying the aerosol canister 16 and the power source 120 may include a switch or operate in connection with a switch that is activated when the chassis 93 is properly seated within the cartridge body 90 of the removable cartridge 14 with the valve stem 17 of the canister properly engaging the stem support 102.

With continued reference to FIGS. 1 and 2, the base housing 12 may further include a display screen 13 (e.g., LCD screen) electrically coupled to the main PCB of the control system, such as, for example, by a flexible ribbon cable, for displaying information in connection with the use of the aerosol delivery unit 10, including, for example, a remaining dose count reflecting the number of doses remaining in the aerosol canister 16 of the removable cartridge 14. The display screen 13 may be powered by the power source 120 carried by the removable cartridge 14 and managed by a power management module located on the main PCB or other PCB component.

The control system may also include a wireless communication module (e.g., Bluetooth module), which may be integrated with the main PCB or other PCB component, for exchanging information with a remote device, such as, for example, a smart phone or other computing device. In this manner, various data, including dose information, may be communicated to the remote device for various purposes, as described in more detail elsewhere.

The base housing 12 may further include one or more external control devices 130 (e.g., buttons, switches, touch controls) for controlling one or more ancillary functions. For example, in some embodiments, a push-button control may be provided for triggering a priming function in which the canister 16 is actuated at least once by the actuator assembly prior to actuation of the canister 16 in response to breath actuation by the user. In other embodiments, the base housing 12 may be completely devoid of any external controls and the aerosol delivery unit 10 may function entirely via spatial manipulation of the aerosol delivery unit 10 and user-interaction with the mouthpiece 15.

With reference to the embodiment of the aerosol delivery unit shown in FIGS. 3A through 9, the removable cartridge 214 may include a canister chassis 293 that is removably coupleable to a mouthpiece subassembly 295 to, among other things, facilitate cleaning of the mouthpiece subassembly 295, and in particular the inhalation passageway 296 and the discharge passageway 300 which extends through the stem support 302. Furthermore, the canister chassis 293 may include a chassis body 307 and one or more additional body portions, such as a chassis cap 308, coupleable together to retain the aerosol canister 216 and other components within the removable cartridge 214. Advantageously, the other components may include a power source 320 having sufficient capacity to power the actuator assembly 260 and other electronic components of the aerosol delivery unit 210 throughout the usable life of the aerosol canister 216 (i.e., until the aerosol canister 216 is depleted). In this manner, a new power source 320 may be provided with each new removable cartridge 214 to ensure sufficient power capacity to power the aerosol delivery unit 210 without interruption. Although the entire removable cartridge 214 may be replaced periodically with the aerosol canister 216, it is appreciated that in some instances, only the canister chassis 293 may be replaced with the canister 216 and the mouthpiece subassembly 295 may be reused throughout the entire life cycle of the aerosol delivery unit 210 (or for at least several canister replacement cycles). Still further, it is appreciated that in some embodiments the valve stem support 302 and associated discharge passageway 300 extending therethrough may be integrated into the canister chassis 293 (as opposed to the mouthpiece subassembly 295) such that a new discharge passageway 300 may be provided when replacing the canister chassis 293 without replacing the mouthpiece subassembly 295.

In some embodiments, the aerosol canister 216 and the power source 320 may be accommodated in adjacent compartments of the canister chassis 293. In other embodiments, the aerosol canister 216 and the power source 320 may be provided in the same compartment. In some instances, the power source 320 may be shaped to conform around at least a portion of the canister 216 to provide additional space savings and to reduce the overall form factor of the aerosol delivery unit 210.

The removable cartridge 214 may comprise electrical contacts 219 (not visible), such as on a rear facing end of the cartridge 214 for providing power from the power source 320 carried onboard the cartridge 214 to the actuator assembly 260 and other system components provided in the base housing 212 when the cartridge 214 is coupled to the base housing 212 for use. A supplemental PCB 255 (FIGS. 4 and 5) may be provided in the removable cartridge 214 and may be in electrical communication with the power source 320 and the aforementioned electrical contacts.

Although the removable cartridge 214 of the example embodiment of the aerosol delivery unit 210 shown in FIGS. 3A through 9 preferably includes an onboard power source 320 sufficient to power all electronic components of the aerosol delivery unit 210 throughout the usable life of the cartridge 214, in some instances the removable cartridge 214 may lack a power source altogether, or in other instances, may include a low capacity power source sufficient only to provide power for some limited functionality, such as, for example, maintaining an accurate dose count associated with the canister 216. In such instances, a suitable power source, including a replaceable power source or rechargeable power source, may be provided in or integrated with the base housing 212 and the size of the removable cartridge 214 may be reduced to provide a particularly slender or low profile cartridge. For embodiments featuring a rechargeable power source, a separate docking unit or station may be provided for selectively charging the rechargeable power source within the base housing 212.

A dose counter arrangement, including a depressible carriage and a counter switch, may be provided within the removable cartridge 214 so as to count and track the number of doses administered and/or remaining in the removable cartridge 214. The dose counter arrangement may be electrically coupled to the supplemental PCB 255 and a storage device (e.g., non-volatile memory) integrated in the supplemental PCB 255 for storing dose information and optionally communicating the dose information to other portions of the control system 250, including, for example, the PCBs 252, 253 provided in the base housing 212. One or more additional switches may also be provided for ensuring that a dose count is valid only when the system is properly assembled. For example, the canister chassis 293 carrying the aerosol canister 216 and the power source 320 may include a switch or operate in connection with a switch that is activated when the canister chassis 293 is properly seated within the mouthpiece subassembly 295 of the removable cartridge 214 with the valve stem 217 of the canister properly engaging the stem support 302. For example, as shown in FIG. 3C, the canister chassis 293 may include a deformable portion 298 which is configured to deform inwardly as the canister chassis 293 is properly seated in the mouthpiece subassembly 295 to contact a switch that provides a signal indicative of a properly assembled cartridge 214. Certain functionality may be disabled in the absence of such a signal.

With reference to FIGS. 3A through 5, the base housing 212 may further include a display screen 213 (e.g., LCD screen) electrically coupled to the main PCB 152, such as, for example, by a flexible ribbon cable, for displaying information in connection with the use of the aerosol delivery unit 210, including, for example, a remaining dose count reflecting the number of doses remaining in the aerosol canister 216 of the removable cartridge 214. The display screen 213 may be powered by the power source 320 carried by the removable cartridge 214 and managed by a power management module located on the main PCB 252 or the sub PCB 253.

The control system 250 may also include a wireless communication module (e.g., Bluetooth module), which may be integrated with the main PCB 252 or the sub PCB253, for exchanging information with a remote device, such as, for example, a smart phone or other computing device. In this manner, various data, including dose information, may be communicated to the remote device for various purposes, as described in more detail elsewhere.

Figure 10:
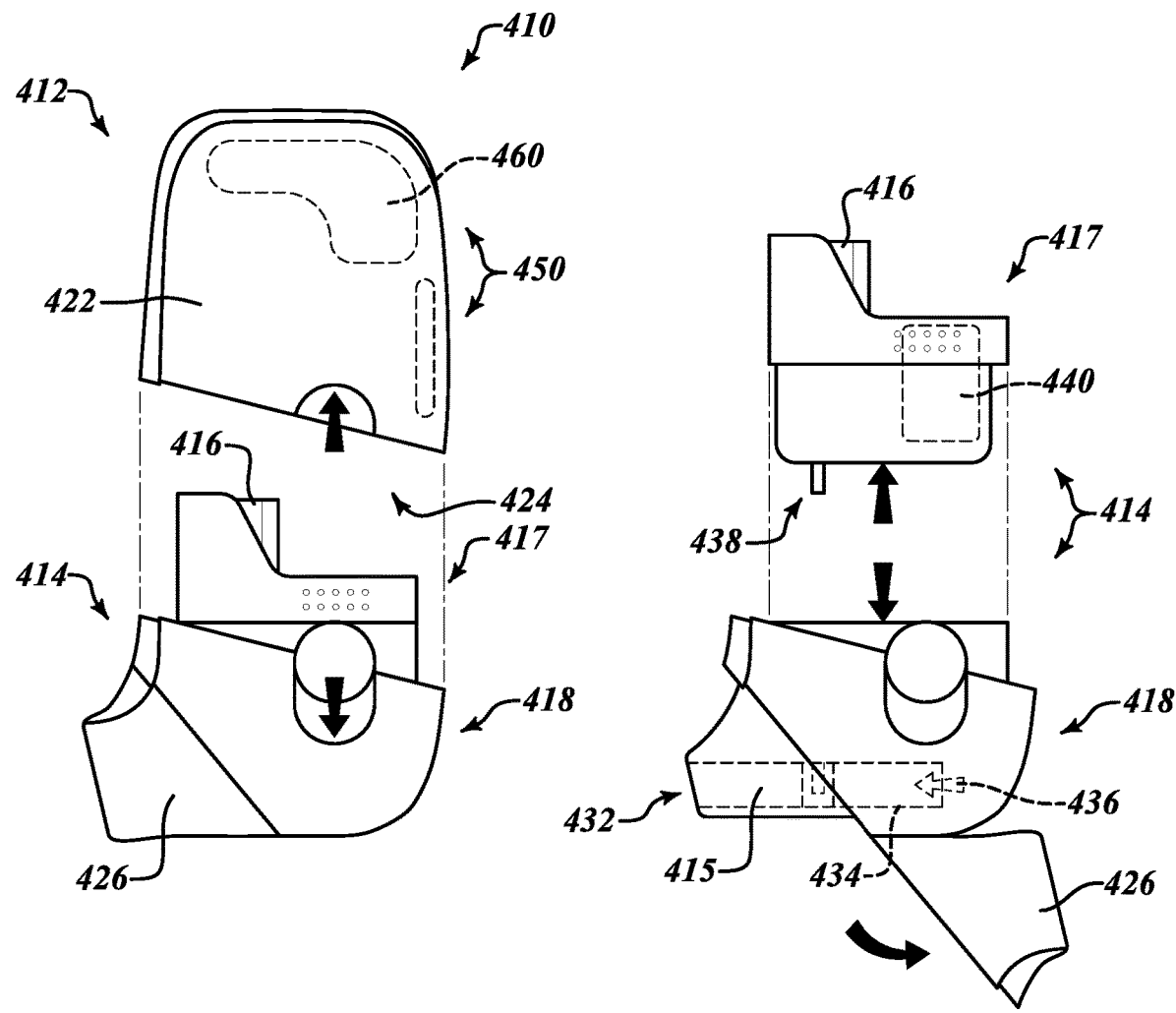
FIG. 10 is a side elevational view showing an aerosol delivery unit, according to another embodiment, having separable portions.

FIG. 10 shows another example of an electronically controlled, motor-driven, breath actuated metered dose inhaler system in the form of a handheld aerosol delivery unit 410. The example aerosol delivery unit 410 is a bottom loading device in which a removable cartridge assembly 414 is insertably receivable in a base housing 412 in a direction generally parallel to a longitudinal axis of an aerosol canister 416 carried by the removable cartridge assembly 414. The base housing 412 may include a housing body 422 defining a cavity 424 within which the removable cartridge assembly 414 may be received. The removable cartridge assembly 414 may comprise a canister chassis 417 that accommodates the canister 416 and a power source 440, and a mouthpiece subassembly 418 that is separable from the chassis 417, the mouthpiece subassembly 418 including a mouthpiece 415 and a cartridge body 430 having a mouthpiece aperture 432, one or more intake apertures 436, and an inhalation passageway 434 extending between the mouthpiece aperture 432 and the one or more intake apertures 436 that is in fluid communication with a discharge outlet 438 of the canister 416 when the removable cartridge assembly 414 is assembled. A mouthpiece cap 426 is provided for selectively revealing and concealing the mouthpiece 415. The base housing 412 may further include a control system 450, including a motor-driven actuation assembly 460, similar to the control system 250 of the embodiment shown in FIGS. 3A through 9. Likewise, the removable cartridge assembly 414 defined by the combination of the canister chassis 417 and the mouthpiece subassembly 418 may include the same or similar features of the removable cartridge 214 of the embodiment shown in FIGS. 3A through 9.

Figure 11:
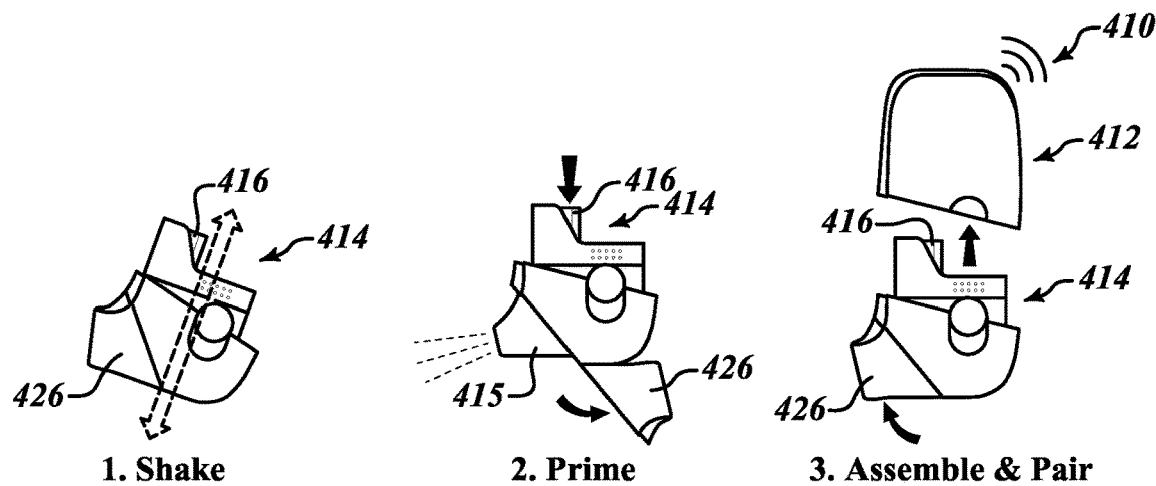
FIG. 11 is a diagram illustrating a method of preparing the aerosol delivery unit of FIG. 10 for use.

FIG. 11 provides a diagram illustrating a method of preparing the aerosol delivery unit 410 for use. The method may begin by shaking or agitating the removable cartridge 414 to prepare the medicament or other matter in the canister 416 for delivery. The method may continue by opening the mouthpiece cap 426 and manually depressing the canister 416 to dispense a dose of aerosolized matter and effectively prime the unit 410 for subsequent use. A user may then insert the removable cartridge 414 into the base housing 412 for subsequent electronically controlled, motor-driven, breath actuated metered dose delivery of the aerosolized matter. Advantageously, assembling the removable cartridge 414 and the base housing 412 together may automatically initiate pairing functionality to connect the aerosol delivery unit 410 wirelessly to an associated smart phone or other computing device.

Figure 12:
FIG. 12 is a diagram illustrating a method of using the aerosol delivery unit of FIG. 10 to receive a dose of aerosolized matter.

FIG. 12 provides a diagram illustrating a method of using the aerosol delivery unit 410 to receive a dose of aerosolized matter. The method may begin by shaking or agitating the delivery unit 410 to prepare the medicament or other matter in the canister 416 for delivery. A user may then open the mouthpiece cap 426 and inhale on the mouthpiece 415 to trigger the control system 450 to drive the actuator assembly 460 to actuate the canister 416 and deliver a first dose of the aerosolized matter during the inhalation. The user may then pause for a short duration (e.g., 30-60 seconds) and repeat the agitation and inhalation steps to receive a second dose of the aerosolized matter. The mouthpiece cap 426 may then be closed and the delivery unit 410 stored for future use.

Figure 13:
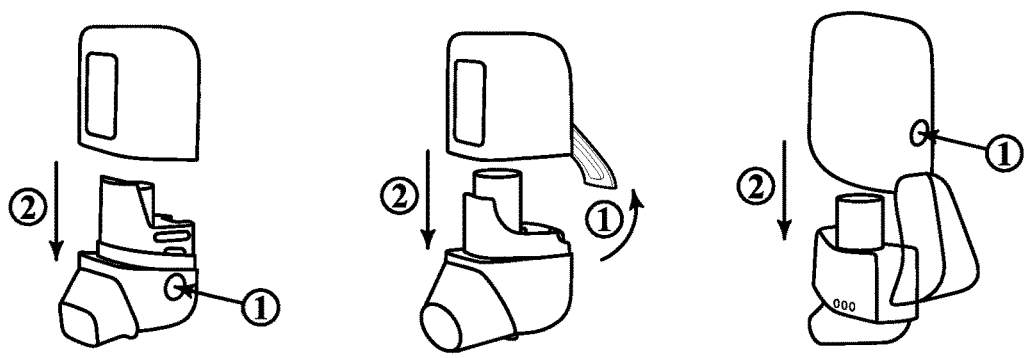
FIG. 13 illustrates aerosol delivery units according to other embodiments having different release mechanisms for releasing a removable cartridge assembly from a base housing.

FIG. 13 illustrates additional example embodiments of electronically controlled, motor-driven, breath actuated metered dose inhaler systems in the form aerosol delivery units each having a removable cartridge assembly selectively releasable from a base housing. As shown, the removable cartridge assembly may be selectively releasable via one or more depressible buttons, manipulable levers or other release mechanisms. More particularly, aerosol delivery unit A illustrates the release of the removable cartridge assembly from the base housing by depressing buttons located on opposing sides of the aerosol delivery unit. Aerosol delivery unit B illustrates the release of the removable cartridge assembly from the base housing by lifting a manipulable lever provided on the back of the aerosol delivery unit. Aerosol delivery unit C illustrates the release of the removable cartridge assembly from the base housing by depressing a single button located on the back of the aerosol delivery unit. Other embodiments may include one or more release mechanisms (buttons, levers, etc.) at other locations, such as, for example, the bottom of the aerosol delivery unit. In other instances, the removable cartridge assembly may be separated from the base housing by simply overcoming a threshold force, such as, for example, may be provided by friction fitted components, detents or other coupling devices. In any event, the removable cartridge assembly may be readily removable from the base housing to facilitate, among other things, replacement of the removable cartridge assembly, cleaning of cartridge components, and/or manual actuation of the canister that is carried by the removable cartridge assembly.

Although embodiments of the aerosol delivery units 10, 210, 410 are depicted herein as front cartridge loading and bottom cartridge loading devices, it is appreciated that a removable cartridge containing, among other things, a canister of matter to be discharged and an associated discharge passageway, may be configured to mate with a base housing containing, among other things, a actuator for firing the canister, from any direction, including, for example, front, bottom, rear and side directions.

Figure 14:
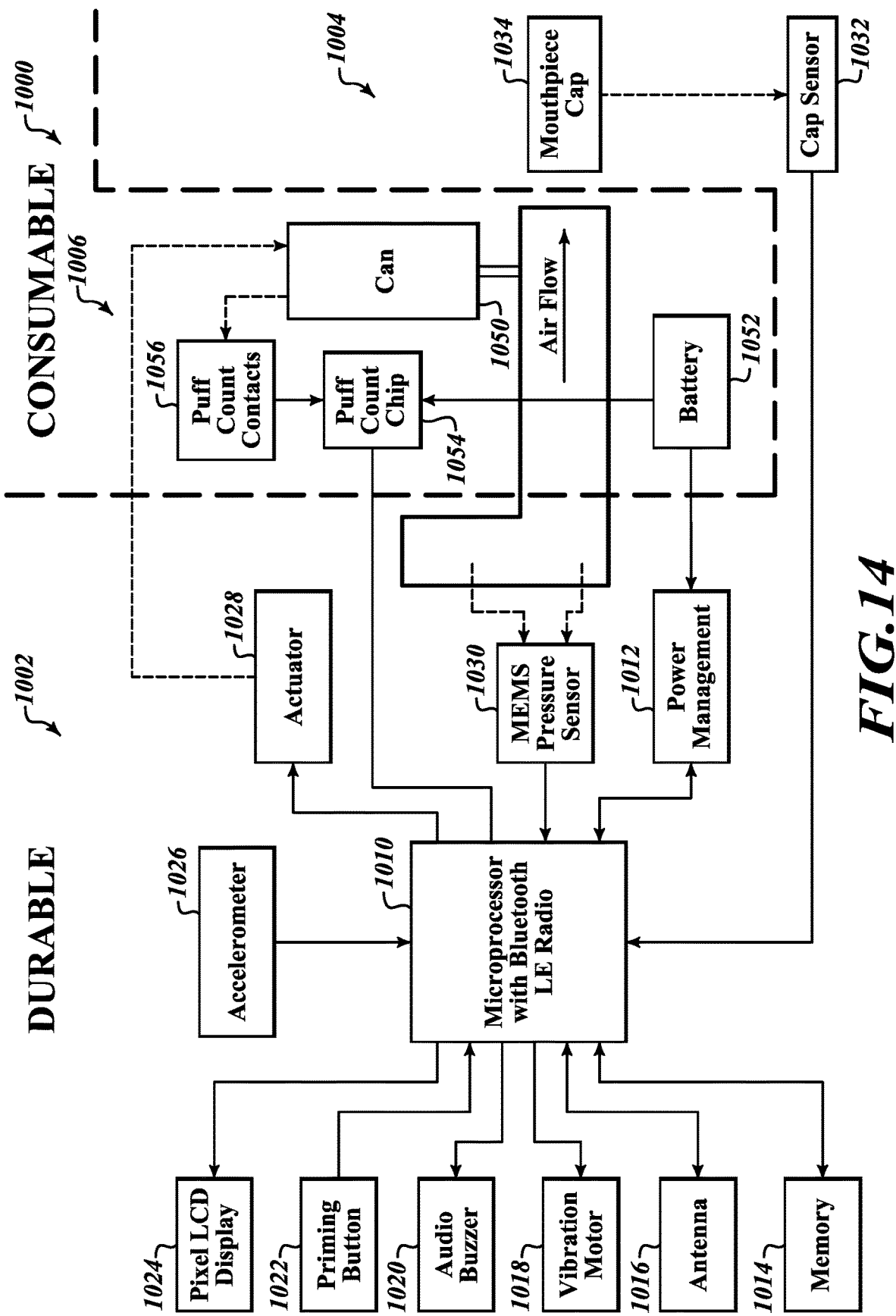
FIG. 14 is a schematic diagram of a control system suitable for use with embodiments of the aerosol delivery units disclosed herein.

Additional features and functionality will now be described with reference to FIG. 14. FIG. 14 schematically depicts a control system 1000 suitable for use with certain embodiments of the aerosol delivery units 10, 210, 410 disclosed herein. In particular, the control system 1000 includes a resident control portion 1002 of an aerosol delivery unit; a mouthpiece control portion 1004; and a consumable cartridge control portion 1006.

In the depicted embodiment, the resident control portion 1002 includes one or more microprocessors 1010 that includes or is communicatively coupled to one or more transmitters (such as a low-energy Bluetooth radio transmitter). In other embodiments, the microprocessor may include or be communicatively coupled to additional transmitter types, or may omit such transmitter. As depicted, the one or more microprocessors 1010 are communicatively coupled to a power management module 1012; one or more memories 1014, such as may store various information and/or processor-executable instructions related to operations of the control system 1000; one or more antennas 1016; a vibration motor 1018, such as may provide vibratory or other tactile feedback for users of the associated aerosol delivery unit; an audio buzzer 1020, such as may provide audio feedback for users of the associated aerosol delivery unit; a user-selectable priming button 1022, such as may allow a user of the associated aerosol delivery unit to manually trigger a priming function; a display 1024, such as to provide visual information or feedback to a user of the aerosol delivery unit; one or more accelerometers 1026, such as may provide data signals to the microprocessor 1010 indicative of an orientation or motion of the aerosol delivery unit; an actuator 1028 for selectively actuating the canister 1050, and a pressure sensor 1030 for sensing air flow arising from inhalation by a user from which to trigger actuation of the canister 1050.

The mouthpiece control portion 1004 includes a mouthpiece cover sensor 1032 communicatively coupled to the one or more microprocessors 1010, and mouthpiece cover 1034, which may be functionally analogous to mouthpiece cover 34 of the example aerosol delivery unit 10 shown in FIG. 1, the mouthpiece cover 234 shown in FIGS. 3A-3C, or the mouthpiece cover 426 shown in FIG. 10.

In the depicted embodiment of FIG. 14, the control system 1000 includes a consumable cartridge control portion 1006 that is removably interfaced with the resident control portion 1002. The consumable cartridge control portion 1006 includes a consumable canister 1050 containing matter (not shown) to be aerosolized; a power source 1052 (which may be functionally analogous to the power source 120 of the example aerosol delivery unit 10 shown in FIGS. 1 and 2, or the power source 320 of the aerosol delivery unit 210 shown in FIGS. 3A through 9)) interfaced with the power management module 1012 of the resident control portion; a dosage quantification or "puff count" chip 1054, which may locally (with respect to the consumable cartridge) track and store information regarding doses of matter expended or remaining within the consumable canister, and is removably interfaced with the one or more microprocessors 1010; and one or more "puff count" contacts 1056 that electromechanically provide signals to the communicatively coupled dosage quantification chip.

In accordance with the control system 1000 of FIG. 14, embodiments may enhance compliance with a dosing regimen by simplifying the inhalation process, providing additional safeguards against improper use of the aerosol delivery unit, and/or by providing targeted information to the user. For example, the control system 1000 may be configured to sense shaking or agitation of the aerosol delivery unit in a period before attempted use via the one or more accelerometers 1026 (or other sensors) and temporarily prevent actuation of the canister 1050 by the actuator 1028 if it is determined that sufficient shaking or agitation has not occurred. The control system 1000 may also provide an indication (e.g., haptic, audible or visual signal) to the user that additional shaking or agitation is required prior to release of the aerosolized matter. As another example, the control system 1000 may be configured to sense an orientation of the aerosol delivery unit in a period before attempted use via the one or more accelerometers 1026 (or other sensors) and temporarily prevent actuation of the canister 1050 by the actuator 1028 if it is determined that the canister 1050 is not properly oriented for delivery of the aerosolized matter (e.g., the aerosol delivery unit is horizontal). The control system 1000 may also provide an indication (e.g., haptic, audible or visual signal) to the user that the aerosol delivery unit must be reoriented to a more vertical position prior to release of the aerosolized matter. Other safeguards may include preventing actuation of the canister 1050 in situations where it is determined that the aerosol delivery unit is not properly assembled, such as, for example, when a removable cartridge carrying the canister 1050 is not properly seated in a base housing comprising the resident control portion 1002. These and other safeguards may collectively enhance compliance with a dosing regimen and help ensure that a user receives a proper dose or medicament or other matter.

Various example graphical user interface ("GUI") screens are now presented with respect to particular embodiments shown for illustrative purposes, although it will be appreciated that other embodiments may include more and/or less information, and that various types of illustrated information may be replaced with other information.

FIGS. 15A-15C depict portions of a Graphical User Interface (GUI) 1100 that may be provided as part of an aerosol delivery system interface to enable various user interactions with a client electronic device that may be, at various times, communicatively coupled to an aerosol delivery unit according to one illustrated embodiment. As depicted, the GUI 1100 is provided by a software application program (or "app") executing on the client electronic device. As used herein, such a client electronic device may be fixed or mobile, and may include instances of various computing devices such as, without limitation, desktop or other computers (e.g., tablets, slates, etc.), network devices, smart phones and other cell phones, consumer electronics, digital music player devices, handheld gaming devices, PDAs, pagers, electronic organizers, Internet appliances, television-based systems (e.g., using set-top boxes and/or personal/digital video recorders), and various other consumer products that include appropriate communication capabilities. In at least some embodiments, the client electronic device may be communicatively coupled to the aerosol delivery unit via a wireless data transport interface of the client electronic device, such as a paired Bluetooth connection, wireless network connection, or other suitable connection.

In the illustrated examples of FIGS. 15A-15C, the GUI interface 1100 includes particular display portions and user-selectable controls that may be presented to user to enable the user to select and define various manners by which client electronic device displays information and interacts with the user's aerosol delivery unit.

In particular, FIG. 15A presents an aerosolized matter identifier 1102, indicating that the matter contained within the consumable canister currently interfaced with the aerosol delivery unit is identified as "Symbicort"; aerosol delivery unit identifier 1104 ("Symbicort Device ID 2"); graphical indicator 1106, providing a visual indication as to a quantity of doses or "puffs" of aerosolized matter remaining within the current consumable canister, along with an indication of the relative percentage of such matter as compared to the total capacity of the consumable canister; time indicator 1108, providing a visual indication of the time elapsed since the most recent prior use of the aerosol delivery unit; user-selectable tab controls 1110*a-d*, allowing a user to access different portions of functionality provided by the aerosol delivery interface system and GUI 1100; and user-selectable assistance control 1112, providing access to one or more instructional pages regarding the GUI 1100 and/or aerosol delivery unit.

FIG. 15B presents various historical tracking information, such as if the user selected tab control 1110*b* of FIG. 15A. In certain embodiments, such information may be generated by the client electronic device based on aerosol delivery data provided by the control system of the communicatively coupled aerosol delivery unit, such as control system 1000 of FIG. 14. In the depicted embodiment of FIG. 15B, the GUI 1100 includes user-selectable chronology controls 1116, enabling the user to select the particular span of time ("1 week," "1 month," or "1 year," respectively) for which historical tracking information is presented; graphical display portion 1118; usage indicator 1120, providing an indication of a quantity and percentage usage of the aerosol delivery unit during the selected time span; dosage information entries 1122*a*, providing information about individual doses consumed by the user during the selected time span; and message indicator 1124, indicating that one or more notifications have yet to be reviewed by the user.

Each of the dosage information entries 1122 indicates a date and time at which the respective dose was delivered via the aerosol delivery unit, as well as whether such dose consisted of a single "puff" or a second such inhalation. In addition, in various embodiments the dosage information entries may provide certain other visual indicia of information associated with the particular dosage entry. For example, dosage information entry 1122*a* includes a flag indicator to denote that only a single inhalation was utilized for that respective dose as well as a user-selectable "+" control to allow the user to view additional information related to the respective dose. Similarly, dosage information entry 1122*b* provides a user-selectable message control, allowing the user to view textual information associated with the entry.

In certain embodiments, the aerosol delivery system interface and/or GUI 1100 may allow the user to select and configure one or more reminders, alerts, or other notifications based on data provided by the communicatively coupled aerosol delivery unit and its associated control system. For example, the user may configure the system interface to provide a reminder within a predetermined time of a scheduled dose; to provide an alert when the user has failed to inhale a dose within a predetermined duration from the last administered dose; to provide one or more notifications regarding a quantity of doses remaining in the currently interfaced consumable canister, such as if a threshold quantity has been exceeded; etc. In at least some embodiments, the user may configure the aerosol delivery system interface to provide such notifications or alerts to other users, such as providing a "shared" notification to one or more family members or medical professionals associated with the user.

FIG. 15C presents shared notification information as part of a Settings control portion, such as if the user selected tab control 1110*d* of FIG. 15A. In the depicted embodiment, the GUI 1100 includes notification type controls 1130 and 1132, indicating notification types currently configured by the user; user-selectable "Add Notification" control 1134, allowing the user to configure additional notification types related to the aerosol delivery unit and aerosol delivery system interface; and user contact control 1136, allowing the user to specify particular contacts to which particular notifications are to be provided by the aerosol delivery system interface.

In the illustrated example of FIG. 15C, the user has configured two types of notifications. The first notification type 1130 indicates that if the user misses a scheduled dose, the aerosol delivery system interface will provide a notification to "Mom" and "Dr. Smith" via text message (as indicated by the highlighted smartphone icon). The second notification type 1132 indicates that upon certain criteria being met regarding the need to refill a prescription (such as if the currently interfaced consumable canister contains less than a predefined quantity of remaining doses, or other configured criteria), the aerosol delivery system interface will provide a notification to "Mom" via email message (as indicated by the highlighted envelope icon). In this and other embodiments, the GUI 1100 may allow the user to configure various other notifications and alerts based on various criteria. For example, such notifications and alerts may be provided at regular time intervals, based on data provided by the aerosol delivery unit, based on information from one or more medical databases (such as if the personalized matter contained within the currently interfaced consumable cartridge passes an expiration date), or based on other information and/or defined criteria.

It will be appreciated that the GUIs, display screens and other information presented with respect to FIGS. 15A-15C are included for illustrative purposes, and that such information and/or other information and associated functionality may be presented or otherwise provided in other manners in other embodiments. In addition, it will be appreciated that GUIs and other information presented to users may vary with the type of client device used by the user, such as to present less information and/or functionality via client devices with smaller display screens and/or less ability to present information to or obtain input from the user, such as under control of a mobile application of the aerosol delivery system interface executing on the client device, or otherwise based on information sent to the client device from the aerosol delivery system.

Although aspects of the embodiments have been described above in connection with a consumable cartridge control portion, it will be appreciated that in some embodiments, the cartridge control portion, or parts thereof, may be non-consumable or durable. In some embodiments, for example, only the canister itself may be consumable while the removable cartridge that accommodates the canister is reusable throughout the life of the aerosol delivery unit.

In accordance with the systems described above, an example method implemented by a processor-based electronic client device may be summarized as including: receiving, by the processor-based electronic client device while communicatively coupled to an aerosol delivery unit and via one or more electronic communications sent over a wireless interface of the electronic client device, aerosol delivery data from the aerosol delivery device, the aerosol delivery data being related to one or more user interactions with the aerosol delivery unit; generating, by the processor-based electronic client device and based at least in part on the received aerosol delivery information, aerosol delivery tracking information regarding the one or more user interactions; and providing, via the processor-based electronic client device, one or more indications regarding at least one of the aerosol delivery tracking information and the aerosol delivery data.

In some instances, providing one or more indications to the user may include displaying, via a user interface of the electronic client device: one or more error messages related to the motion or the orientation of a canister interfaced with the aerosol delivery unit; an indication of estimated battery power remaining to the aerosol delivery unit; one or more reminder notifications regarding a scheduled dose of matter; and/or instructional information regarding use of the aerosol delivery unit. In addition to or in lieu of such displaying on the electronic client device, one or more error messages, indication of battery power remaining and/or instructional use information may likewise be displayed on a screen or other display device of the aerosol delivery unit itself.

In some instances, receiving aerosol delivery data from the aerosol delivery unit may include receiving at least one of a group that includes: data indicative of a motion or orientation of a canister interfaced with the aerosol delivery unit; data identifying matter contained in the canister; data indicative of a quantity of matter remaining in the canister; data indicative of a quantity of matter expended from the canister; data indicative of a number of doses of matter expended from the canister; and data indicative of a number of doses of matter remaining in the canister.

In some instances, receiving aerosol delivery data from the aerosol delivery unit may include receiving data indicative of a quantity of doses of matter expended from the canister, and generating the aerosol delivery tracking information may includes generating a quantity of doses of matter remaining in the canister. In some instances, generating the aerosol delivery tracking information may include generating dosage history information for a user associated with the processor-based electronic client device. Generating the dosage history information may include generating dosage history information based at least in part on one or more canisters previously interfaced with the aerosol delivery unit.

In some instances, the processor-based electronic client device may be associated with a first user, and providing one or more indications may include providing one or more notifications to one or more distinct other users regarding the first user's interactions with the aerosol delivery unit.

In accordance with aspects of the embodiments of the aerosol delivery units disclosed herein, an aerosol delivery system for selectively delivering a dose of aerosolized matter may be summarized as including: an aerosol delivery unit configured to receive a canister containing the matter to be aerosolized; one or more accelerometers; one or more processors; and at least one memory, the memory including instructions that, upon execution by at least one of the one or more processors, cause the aerosol delivery system to provide, via a user interface of a client device associated with a user of the aerosol delivery unit, one or more indications of information related to a canister interfaced with the aerosol delivery unit. The information may include, for example, at least one of a group that includes: a motion or orientation of the canister; a quantity of matter remaining in the canister, a quantity of matter expended from the canister, a number of doses of matter expended from the canister, and an estimated number of doses of matter remaining in the canister. The indicated information may further include one or more identifiers associated with matter contained in the canister.

In some instances, the instructions may further cause the associated client device or a display of the aerosol delivery unit to display one or more error messages related to the motion or the orientation of the canister; an indication of estimated battery power remaining to the aerosol delivery unit; one or more reminder notifications regarding a scheduled dose of matter; and/or instructional information regarding use of the aerosol delivery unit. Other features and functionality will be readily apparent by one of ordinary skill in the relevant art upon reviewing the present disclosure.

Moreover, aspects and features of the various embodiments described above may be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

This application claims priority to U.S. Provisional Application No. 62/194,701, filed Jul. 20, 2015, and U.S. Provisional Application No. 62/212,379, filed Aug. 31, 2015, which applications are incorporated herein by reference in their entireties.

The invention claimed is:

1. An aerosol delivery unit for selectively delivering a dose of aerosolized matter, the aerosol delivery unit comprising:
a removable cartridge comprising a canister and a mouthpiece from which to receive the dose of aerosolized matter, the canister having a canister body containing the matter to be aerosolized and a valve stem movable relative to the canister body to release the dose of aerosolized matter from the canister;
a base housing configured to insertably receive the removable cartridge; and
an actuator assembly accommodated within the base housing that interfaces with the canister when received therein to control movement of the canister body relative to the valve stem, the actuator assembly including a motor and a motor-driven actuator that is operatively coupled to the motor and configured to engage the canister to move the canister body relative to the valve stem throughout an entirety of actuation of the canister in direct relation to a rotational position of the motor, and
wherein the actuator assembly is powered by a power source carried by the removable cartridge.

2. The aerosol delivery unit of claim 1, further comprising:
a control system, the control system configured to control actuation of the canister throughout dose delivery via the actuator assembly in response to a pressure signal arising from inhalation of a user via the mouthpiece of the removable cartridge.

3. The aerosol delivery unit of claim 1 wherein the motor-driven actuator comprises a rotatable cam member and a yoke that is urged into contact with the rotatable cam member, the rotatable cam member controlling a position of the yoke throughout the entirety of actuation of the canister in direct relation to the rotational position of the motor.

4. The aerosol delivery unit of claim 3 wherein the yoke is operatively coupled to the motor by a motor-driven arrangement including the rotatable cam member and a gear train having a worm gear set.

5. The aerosol delivery unit of claim 4 wherein the worm gear set includes a worm screw having an axis of rotation parallel to an axis of rotation of the motor and a worm wheel meshed with the worm screw, and wherein the rotatable cam member and the worm wheel are portions of the same unitary part.

6. The aerosol delivery unit of claim 5 wherein a driven spur gear is provided at one end of the worm screw and is meshed with a corresponding drive spur gear coupled to the motor, the driven spur gear and the drive spur gear having a gear ratio of at least 2:1.

7. The aerosol delivery unit of claim 3 wherein the yoke is biased into direct contact with the rotatable cam member throughout the entirety of actuation of the canister by one or more bias members.

8. The aerosol delivery unit of claim 7 wherein the actuator assembly includes a casing and the one or more bias members are provided between the casing and the yoke.

9. The aerosol delivery unit of claim 3 wherein the actuator assembly includes a casing and the yoke is constrained by the casing to move linearly as the rotatable cam member rotates to actuate the canister.

10. The aerosol delivery unit of claim 1 wherein the removable cartridge comprises a mouthpiece aperture formed in the mouthpiece through which to inhale the dose of aerosolized matter released from the canister, a plurality of inhalation passageway intake orifices through which to draw in air from an environment surrounding the aerosol delivery unit, and an inhalation passageway extending from a location of the inhalation passageway intake orifices to a location of the mouthpiece aperture.

11. The aerosol delivery unit of claim 10, further comprising a pressure sensor arranged to detect pressure within the inhalation passageway via a location near the plurality of intake orifices, wherein a change in the pressure is indicative of one or more characteristics of a flow of air moving through the plurality of intake orifices.

12. The aerosol delivery unit of claim of claim 11 wherein the pressure sensor is carried by the base housing and configured to interface with the removable cartridge when the removable cartridge is received in the base housing.

13. The aerosol delivery unit of claim 12, further comprising:
a compliant seal positioned to engage the removable cartridge and provide a sealed passageway extending between the pressure sensor and the inhalation passageway of the removable cartridge.

14. The aerosol delivery unit of claim 10 wherein the plurality of inhalation passageway intake orifices consist of a respective orifice positioned on each of opposing sides of the aerosol delivery unit.

15. The aerosol delivery unit of claim 10 wherein the removable cartridge includes a cartridge body defining at least a majority of the inhalation passageway and defining the plurality of intake orifices.

16. The aerosol delivery unit of claim 15 wherein the cartridge body further includes a sensor passageway for providing fluid communication between the inhalation passageway and the pressure sensor.

17. The aerosol delivery unit of claim 16 wherein the base housing includes a complementary sensor passageway that interfaces with the sensor passageway of the cartridge body.

18. The aerosol delivery unit of claim 15 wherein the plurality of intake orifices extend through a floor of the cartridge body.

19. The aerosol delivery unit of claim 1 wherein the removable cartridge further comprises a cartridge unit within which the canister is loaded, the cartridge unit including a cartridge body having a mouthpiece aperture through which to inhale the dose of aerosolized matter released from the canister, one or more intake apertures through which air can enter the cartridge unit, and an inhalation passageway extending from a location of the one or more intake apertures to a location of the mouthpiece aperture and being in fluid communication with a discharge outlet of the canister, and
wherein the power source is carried by the cartridge body for powering the actuator assembly provided in the base housing adjacent the removable cartridge.

20. The aerosol delivery unit of claim 19 wherein a pressure sensor is provided within the base housing and arranged to detect pressure within the inhalation passageway of the cartridge body of the removable cartridge, and wherein the pressure sensor is supported by a printed circuit board powered by the power source of the removable cartridge.

21. The aerosol delivery unit of claim 19 wherein a wireless communication device is provided within the base housing to transmit information pertaining to the delivery of the aerosolized matter, the wireless communication device being powered by the power source of the removable cartridge.

22. The aerosol delivery unit of claim 19 wherein the cartridge unit comprises a chassis that accommodates the canister and the power source, and a mouthpiece subassembly that is separable from the chassis, the mouthpiece subassembly including the cartridge body having the mouthpiece aperture, the one or more inhalation passageway intake apertures, and the inhalation passageway.

23. The aerosol delivery unit of claim 22 wherein the cartridge unit further comprises a dose counting arrangement enclosed within the chassis that accommodates the canister and the power source.

24. The aerosol delivery unit of claim 22 wherein the cartridge unit includes a switch device arranged to generate an indication when the chassis that accommodates the canister and the power source is properly coupled to the mouthpiece subassembly.

25. The aerosol delivery unit of claim 1 wherein the base housing includes an electronic display from which to display information pertaining to the delivery of the aerosolized matter, the display being powered by the power source of the removable cartridge.

26. The aerosol delivery unit of claim 1 wherein a cavity of the base housing is sized and shaped to receive the removable cartridge in a front loading direction or a bottom loading direction.

27. The aerosol delivery unit of claim 1 wherein the removable cartridge is selectively releasable from the base housing via one or more user accessible release mechanisms.

28. The aerosol delivery unit of claim 1 wherein the removable cartridge comprises electrical contacts for interfacing with a control system of the base housing and providing power from the power source onboard the removable cartridge to the actuator assembly provided in the base housing.

* * * * *